United States Patent [19]
Kobayashi et al.

[11] Patent Number: 5,188,829
[45] Date of Patent: Feb. 23, 1993

[54] RAPIDLY ACTING PROUROKINASE

[75] Inventors: Yo-ichi Kobayashi, Odawara; Muneki Omori, Toshima; Chikako Yamada, Ebina, all of Japan

[73] Assignees: Sagami Chemical Research Center, Tokyo; Central Glass Company, Limited, Yamaguchi; Hodogaya Chemical Co., Ltd., Tokyo; Nippon Soda Company, Limited, Tokyo; Nissan Chemical Industries, Limited, Tokyo; Tosoh Corporation, Yamaguchi, all of Japan

[21] Appl. No.: 340,007

[22] PCT Filed: Aug. 18, 1988

[86] PCT No.: PCT/JP88/00815
§ 371 Date: Apr. 10, 1989
§ 102(e) Date: Apr. 10, 1989

[87] PCT Pub. No.: WO89/01513
PCT Pub. Date: Feb. 23, 1989

[30] Foreign Application Priority Data
Aug. 19, 1987 [JP] Japan .................. 62-204149

[51] Int. Cl.$^5$ ............ A61K 37/547; C12N 9/72; C12N 15/52
[52] U.S. Cl. ................ 424/94.63; 435/215; 435/226; 435/172.3
[58] Field of Search ............ 435/215, 226, 252.33, 435/172.3, 320.1; 424/94.63

[56] References Cited
FOREIGN PATENT DOCUMENTS
092182 10/1983 European Pat. Off. .
200451 11/1986 European Pat. Off. .
0210279 2/1987 European Pat. Off. .
56-158799 12/1981 Japan .
59-51300 3/1984 Japan .
62-143686 6/1987 Japan .

OTHER PUBLICATIONS
Nelles et al., J. Biol. Chem. 262(2):5682–5689 (1987).
Ichinov et al., J. Biol. Chem. 261(8):3486–3489 (1986).
Pozsgay et al., Eur. J. Biochem., 115, pp. 491–495 (1981).
Chang et al., Eur. J. Biochem., 151, pp. 217–224 (1985).
Kasai et al., J. Biol. Chem., vol. 260, No. 22 pp. 12382–12389 (1985).
Wun et al., J. Biol. Chem., vol. 257 No. 12, pp. 7262–7268 (1982).
Kaminski et al., J. of Biol. Chem., vol. 258, No. 17, pp. 10530–10535 (1983).
Lin et al., Journal Biol. Chem., vol. 254, No. 20, pp. 10421–10425 (1979).

Primary Examiner—Richard A. Schwartz
Assistant Examiner—Nancy T. Vogel
Attorney, Agent, or Firm—Wegner, Cantor, Mueller & Player

[57] ABSTRACT

A human prourokinase-like polypeptide having the following amino acid sequence:

$$(Met).Ser^1 - X^{156}.Y^{157}.Z^{158} -$$

wherein Met is an occasionally present methionine, Ser is the first N-terminal serine, X is the 156th arginine or other amino acid, Y is the 157th proline, glycine, alanine or valine, Z is the 158th lysine or arginine, and the solid lines represent the same amino acid sequences as corresponding parts of an amino acid sequence of a natural type human prourokinase or a human prourokinase-like polypeptide wherein the 135th lysine is changed to an amino acid other than a basic amino acid, or substantially the same amino acid sequence as the above-mentioned amino acid sequence, is provided.

Moreover, a DNA segment coding for the above-mentioned polypeptide; a plasmid containing the DNA segment; *E. coli* transformed with the plasmid; a process for production of the polypeptide characterized by culturing the *E. coli*; a pharmaceutical preparation containing the polypeptide; use of the polypeptide for prophylaxis or treatment of thrombus formation; and use of the polypeptide for the production of pharmaceutical preparation used for that purpose.

4 Claims, 18 Drawing Sheets

Fig. 1-1

```
CAGGCGCCGGCTCGGCCCCTTCTGCGCCACCGAGCCGCCGTCTAGCGCCCCGACCTCGCCACC
50 met arg ala leu leu ala arg leu    8
                                              ATG AGA GCC CTG CTG GCG CGC CTG    1
                                                1 leu leu cys val leu val val ser asp ser lys gly SER ASN GLU LEU HIS GLN VAL PRO SER ASN CYS ASP CYS   13
CTT CTC TGC GTC CTG GTC GTG TCC GAC AGC AAG GGC AGC AAT GAA CTT CAT CAA GTT CCA TCG AAC TGT GAC TGT
               100                                                  150

LEU ASN GLY THR CYS VAL SER ASN LYS TYR PHE SER ASN ILE HIS TRP CYS ASN CYS PRO LYS LYS PHE GLY    38
CTA AAT GGA ACA TGT GTG TCC AAC AAG TAC TTC TCC AAC ATT CAC TGG TGC AAC TGC CCA AAG AAA TTC GGA
                          200                                             250

GLY GLN HIS CYS GLU ILE ASP LYS SER LYS THR CYS TYR GLU GLY ASN GLY HIS PHE TYR ARG GLY LYS ALA SER    63
GGG CAG CAC TGT GAA ATA GAT AAG TCA AAG ACC TGT TAT GAG GGA AAT GGT CAC TTT TAC CGA GGA AAG GCC AGC
                              250                                                   300

THR ASP THR MET GLY ARG PRO CYS LEU PRO TRP ASN SER ALA THR VAL LEU GLN THR TYR HIS ALA HIS ARG    88
ACT GAC ACC ATG GGC AGG CCC TGC CTG CCC TGG AAC TCT GCC ACT GTC CTT CAG ACG TAC CAT GCC CAC AGA
                              300                                                   350

SER ASP ALA LEU GLN LEU GLY LEU GLY LYS HIS ASN TYR CYS ARG ASN PRO ASP ASN ARG ARG ARG PRO TRP CYS  113
TCT GAT GCT CTT CAG CTT GGC CTG GGG AAA CAT AAT TAC TGC AGG AAC CCA GAC AAC CGG AGG AGG CCA TGG TGC
                        400                                                   450

TYR VAL GLN VAL GLY LEU LYS LYS LEU PRO VAL GLN GLU CYS MET VAL HIS ASP CYS ALA ASP GLY LYS LYS PRO SER  138
TAT GTG CAG GTG GGC CTA AAG AAG CTT CCG GTC CAA GAG TGC ATG GTG CAT GAC TGC GCA GAT GGA AAA AAG CCC TCC
                              500
```

Fig. 1-2

```
SER PRO PRO GLU LEU LYS PHE GLN CYS GLY GLN LYS THR LEU ARG PRO ARG PHE LYS ILE ILE GLY GLY GLU 163
TCT CCT CCA GAA TTA AAA TTT CAG TGT GGC CAA AAG ACT CTG AGG CCC CGC TTT AAG ATT ATT GGG GGA GAA
                550                                 600

PHE THR THR ILE GLU ASN GLN PRO TRP PHE ALA ALA ILE TYR ARG ARG HIS ARG GLY GLY SER VAL THR TYR VAL 188
TTC ACC ACC ATC GAG AAC CAG CCC TGG TTT GCG GCC ATC TAC AGG AGG CAC CGG GGG TCT GTC ACC TAC GTG
                            650

CYS GLY SER LEU ILE SER PRO CYS TRP VAL ILE SER ALA THR HIS CYS PHE ILE ASP TYR PRO LYS LYS GLU 213
TGT GGA GGC CTC ATC AGC CCT TGC TGG GTG ATC AGC GCC ACA CAC TGC TTC ATT GAT TAC CCA AAG AAG GAG
                700                                 750

ASP TYR ILE VAL TYR LEU GLY ARG SER ARG LEU ASN SER ASN THR GLN GLY GLU MET LYS PHE GLU VAL GLU ASN 238
GAC TAC ATC GTC TAC CTG GGT CGC TCA AGG CTT AAC TCC AAC ACG CAA GGG GAG ATG AAG TTT GAG GTG GAA AAC
                            800

LEU ILE LEU HIS LYS ASP TYR SER ALA ASP THR LEU ALA HIS HIS ASN ASP ILE ALA LEU LEU LYS ILE ARG SER 263
CTC ATC CTA CAC AAG GAC TAC AGC GCT GAC ACG CTT GCT CAC CAC AAT GAC ATT GCC CTT CTG AAG ATC CGT TCC
                850                                 900

LYS GLU GLY ARG CYS ALA GLN PRO SER ARG THR ILE GLN THR ILE CYS LEU PRO SER MET TYR ASN ASP PRO GLN 288
AAG GAG AGG TGT GCG CAG CCA TCC CGG ACT ATA CAG ACC ATC TGC CTG CCC TCG ATG TAT AAC GAT CCC CAG
                            950

PHE GLY THR SER CYS GLN ILE THR GLY PHE GLY LYS GLU ASN SER THR ASP TYR LEU TYR PRO GLU GLN LEU LYS 313
TTT GGC ACA AGC TGT CAG ATC ACT GGC TTT GGA AAA GAG AAT TCT ACC GAC TAT CTC TAT CCG GAG CAG CTG AAA
                1000                                1050
```

Fig. 1-3

```
MET THR VAL VAL LYS LEU ILE SER HIS ARG GLU CYS GLN GLN PRO HIS TYR TYR GLY SER GLU VAL THR THR LYS 338
ATG ACT GTT GTG AAG CTG ATT TCC CAC CGG GAG TGT CAG CAG CCC CAC TAC TAC GGC TCT GAA GTC ACC ACC AAA
                                            1100

MET LEU CYS ALA ALA ASP PRO GLN TRP LYS THR ASP SER CYS GLN GLY ASP SER GLY GLY PRO LEU VAL CYS SER 363
ATG CTG TGT GCT GCT GAC CCA CAG TGG AAA ACA GAT TCC TGC CAG GGA GAC TCA GGA GGA CCC CTC GTC TGT TCC
                        1150                                        1200

LEU GLN GLY ARG MET THR LEU GLY ILE VAL SER TRP GLY ARG GLY CYS ALA LEU LYS ASP LYS PRO GLY VAL 388
CTC CAA GGC CGC ATG ACT TTG GGA ATT GTG AGC TGG GGC CGT GGA TGT GCC CTG AAG GAC AAG CCA GGC GTC
                            1250

TYR THR ARG VAL SER HIS PHE LEU PRO TRP ILE ARG SER HIS THR LYS GLU GLU ASN GLY LEU ALA LEU XXX 411
TAC ACG AGA GTC TCA CAC TTC TTA CCC TGG ATC CGC AGT CAC ACC AAG GAA GAG AAT GGC CTG GCC CTC TGA GGG
                1300                                    1350

TCCCCAGGGAGGAAACGGGCACCACCCCGCTTCTTGCTGGTTGCTGTTGCAGTAGCTCATCCATCAGCTGTAAGAGACTGGGAAGATAGGCT
                                1400                                    1450

CTGCACAGATGGATTTGCCTGTGCCCACCAGGGGAACGACAATAGCTTTACCCTCAGGCATAGCCTTGTCTTTTCTCGACTGAAGCCTGCCAGACCCCTCTGCC
        1500                                1550

AGGATGGAGGGGTGTCCTGACTCAACATGTTACTGACCAGCAACTGTCTTTTCTCGACTGAAGCCTGGAGAGTTAAAAAGGGCAGGCCATCTCCT
        1600                                1650

GTGCATGGGCTCGAAGGAGAGCCAGCTCCCCGAGCGGTGGGCATTGTGAGGCCCATGGTTGAGAAATGAATAATTCCAATTAGGAAGTGTAAGC
        1700                                1750
```

Fig. 1-4

```
AGCTGAGGTCTCTTGAGGAGCTTAGCCAATGTGGGAGCAGAGACACTAACGACTTCAGGGACCAGGCCTCTGATATTCCATGAAT
                                                                              1800                                          1850
GTATCAGGAAATATATGTGTGTATGTTTGCACACTTGTGTGCCTGTGAGTTAAGTGTGAGAAAGAGCTGGTGTGTCTGATTGTTAAGTCTAAA
                                                                              1900                                          1950
TATTTCCTTAAACTGTGTGACTGGTCCTTTCTGGAGAGTTATAGGTCACTCCCTGGGCCCTCTTGGGAGGTTATAGGTCACTCCCACGTGACAG
                                                                              2000                                          2050
TGCCTGGAAATGTATTATTCTGCAGCATGACCTGTGACCAGCACTGTCTCAGTTTCACTTTCACATAGATGCCCTTTCTGGCCAGTTATCCCTCCT
                                                                              2100                                          2150
TTTAGCCTAGTTCATCCAATCCTCACTGGGTGGGGTGAGGACCACTCCCGTACACTGAATATTTATATTTCACTATTTTTATTTATATTTTGTAATTT
                                                                              2200                                          2250
TAAATAAAAGTGATCAATAAAATGTGATTTTTCTGATGAAAAA
                                         2294
```

EcoRI (Partial digestion)
Klenow Fragment
T4 DNA Ligase

BamHI (Partial digestion)
NarI/Klenow Fragment
T4 DNA Ligase

Eco 47III
PstI ( Partial Fraction )
T₄ DNA Ligase

Fig. 4-1

```
             Pro Arg Pro Lys Ile Ile Gly Gly
TUK-RPK(A) 5' G CCT AGG CCG AAA ATT ATT GGT GGT G    3'
TUK-RPK(B) 3'   A TCC GGC TTT TAA TAA CCA CCA CTT AA 5'

Pro Arg Pro Arg Ile Ile Gly Gly
TUK-RPR(A) 5' G CCT CGT CCT CGA ATT ATT GGT GGT G    3'
TUK-RPR(B) 3'   A GCA GCA GCT TAA TAA CCA CCA CTT AA 5'

Pro Gln Pro Arg Ile Ile Gly Gly
TUK-QPR(A) 5' G CCT CAG CCG CGG ATT ATT GGT GGT G    3'
TUK-QPR(B) 3'   A GAC GGC GCC TAA TAA CCA CCA CTT AA 5'

Pro Ser Gly Arg Ile Ile Gly Gly
TUK-SGR(A) 5' G CCT AGC GGC CGG ATT ATT GGT GGT G    3'
TUK-SGR(B) 3'   A TCG CCG GCC TAA TAA CCA CCA CTT AA 5'
```

Synthetic DNA oligomer used for mutagenesis

Fig. 4-2

```
                  Pro  X   Gly Lys Ile Ile Gly Gly
TUK-XGK(A)  5'  G CCT N_XA GGC AAA ATT ATT GGT GGT G   3'
TUK-XGK(B)  3'       A N_XB CCG TTT TAA TAA CCA CCA CTT AA  5'

Pro  X   Ala Lys Ile Ile Gly Gly
TUK-XAK(A)  5'  G CCT N_XA GCC AAA ATT ATT GGT GGT G   3'
TUK-XAK(B)  3'       A N_XB CGG TTT TAA TAA CCA CCA CTT AA  5'

Pro  X   Ala Arg Ile Ile Gly Gly
TUK-XAR(A)  5'  G CCT N_XA GCC CGG ATT ATT GGT GGT G   3'
TUK-XAR(B)  3'       A N_XB CGG GCC TAA TAA CCA CCA CTT AA  5'

Pro  X   Val Lys Ile Ile Gly Gly
TUK-XVK(A)  5'  G CCT N_XA GTC AAA ATT ATT GGT GGT G   3'
TUK-XVK(B)  3'       A N_XB CAG TTT TAA TAA CCA CCA CTT AA  5'
```

Exemplified synthetic DNA oligomer useful for mutagenesis

Fig. 4-3

```
              Pro  X   Val Arg Ile Ile Gly Gly
TUK-XVR(A) 5' G CCT N_XA GTC CGG ATT ATT GGT GGT G   3'
TUK-XVR(B) 3'   A N_XB CAG GCC TAA TAA CCA CCA CTT AA 5'
```

Exemplified synthetic DNA oligomer useful for mutagenesis

Lane 1  Molecular weight marker ( Bio-Rad )
   2    Mutant Prourokinase Q-RPK, 1000 IU
   3    Mutant Prourokinase Q-RPR, 1000 IU
   4    Natural type prourokinase, 1000 IU
   5    Mutant prourokinase Q( 135 ) D( 157 ), 1000 IU SDS-Polyacrylamide gel electrophoresis
pattern for purified prourokinase preparation Activation by plasmin with elapse of time
( 5 IU prourokinase/$3 \times 10^{-4}$ CU plasmin )

Activation by thrombin with elapse of time
( 4 IU prourokinase/$4 \times 10^{-4}$ NIHU thrombin )

Residual activity after thrombin-treatment time
( .4 IU prourokinase/4×10$^{-4}$ NIHU thrombin )

RAPIDLY ACTING PROUROKINASE

TECHNICAL FIELD

The present invention relates to rapidly acting human-prourokinase-like polypeptides, DNA segments coding for the polypeptide, plasmids containing the DNA segment, *Escherichia coli* containing the plasmid, a process for the production of human prourokinase-like polypeptides using the *E. coli*, and the use of the polypeptides.

BACKGROUND ART

Human urokinase is an enzyme found as a trace in human urine capable of activating inactive plasminogen into plasmin, and the plasmin thus formed is capable of dissolving fibrin. This urokinase consists of two polypeptide chains linked together by a disulfide bond. On the contrary, human prourokinase is a single chain polypeptide in which the aforesaid two polypeptide chains are joined together through an amide bond. Although this prourokinase itself does not possess the aforementioned activity, it can be converted to the preceding active urokinase by cutting one amide bond.

Japanese Patent Application No. 61-12984 (Japanese Unexamined Patent Publication No. 62-143686) (EP 0210279) discloses stabilized human prourokinase-like polypeptides wherein the 135th amino acid and the 157th amino acid are varied, but these are intended to inhibit a cleavage between the 135th amino acid and the 136th amino acid, and/or a cleavage between the 158th amino acid and the 159th amino acid, and therefore, are completely different from the polypeptides of the present invention.

Both the prourokinase described in EP 0200451 and the prourokinase-like polypeptides described in Japanese Patent Application No. 61-12984 (Japanese Unexamined Patent Publication No. 62-143686) (EP 0210279) do not practically exhibit the activities thereof at a site at which thrombus is present, and therefore it is assumed that, even though applied in a large amount, side effects such as systemic hemorrhage are prevented. Nevertheless, it is considered that the conversion rate thereof to a two chain type is low.

As described above, the human urokinase is an activated enzyme, and the activity thereof is rapidly lost due to the presence of a large amount of various inhibitors in blood, and therefore, where used as a therapeutic agent, a large amount thereof must be administered. As a result, a side effect of a systemic formation of plasmin occurs, which tends to cause systemic hemorrhage.

Although prourokinase, also called single-chain urokinase, is usually inactive in plasma, it exhibits a weak activity at a site at which thrombus is present, to convert plasminogen to plasmin. It is considered that, since a small amount of plasmin produced by the action of a tissue plasminogen activator or prourokinase converts prourokinase to a two-chain type high molecular weight urokinase having a high activity, the conversion of plasminogen to plasmin rapidly proceeds, and the thrombus is lyzed (literature 1).

Where prourokinase is used as thrombolytic agent, a small application amount does not produce a sufficient amount of plasmin, and therefore, the thrombus cannot be efficiently lyzed. Conversely, in the case of an excess application amount, even though a large amount of plasmin is temporarily produced, an increased amount of the plasmin does not increase the thrombolysis, due to the distance thereof from a thrombus site, resulting in a decreased thrombolysis efficiency. Moreover, a portion of plasmin thus produced is inactivated by inhibitors such as $\alpha_2$-antiplasmin, and another portion activates prourokinase at a site at which thrombus is not present, resulting in side effects such as systemic hemorrhage. Therefore, when administering prourokinase, a dose and manner of administration which will not produce a temporal excess amount of plasmin is described. Moreover, it is reported that prourokinase, when cleaved at a peptide bond between Arg 156 and Phe 157, is no longer activated by plasmin (literature 2), and accordingly, the prourokinase cannot properly exhibit its function in the presence of thrombin.

EP 0200451 describes protease-resistant urokinases wherein the 156th to 158th amino acids are changed, but all of these urokinases are intended only to prevent protease cleavage at a site between the 158th amino acid and the 159th amino acid, on the assumption that the cleavage of this site is not necessary when activating prourokinase, and accordingly, are completely different from the present polypeptides.

Accordingly, a new type of human prourokinase is sought which, while maintaining a high thrombus specificity of human prourokinase, does not exhibit side effects due to a large application amount, is rapidly activated during and after the formation of thrombus, and therefore, does not have the above-mentioned disadvantages of human urokinase, human prourokinase, and aforementioned derivatives thereof. Such a human prourokinase is not known.

DISCLOSURE OF THE INVENTION

Accordingly, the present invention provides human prourokinase-like polypeptides which have a higher specificity to thrombus in comparison with a natural type human prourokinase when administered to an organism, do not exhibit side effects when administered in a large amount, are activated by thrombin, have an improved rapid action, and preferably are difficult to inactivate by a cleavage at a site between the 156th amino acid and the 157th amino acid by thrombin; a gene system for the production of the polypeptide and a process for production of the polypeptide using the gene system; and the use of the polypeptide.

More specifically, the present invention provides a human prourokinase-like polypeptide having the following amino acid sequence:

(Met)-Ser$^1$—X$^{156}$.Y$^{157}$.Z$^{158}$ wherein Met is an occasionally present methionine, Ser is the first N-terminal serine, X is the 156th arginine or other amino acid, Y is the 157th proline, glycine, alanine or valine, Z is the 158th lysine or arginine, and the solid lines are the same amino acid sequences as corresponding parts of an amino acid sequence of a natural type human prourokinase or a human prourokinase-like polypeptide wherein the 135th lysine is changed to an amino acid other than a basic amino acid, or has substantially the same amino acid sequence as the above-mentioned amino acid sequence.

The present invention also provides a DNA segment coding for the above-mentioned human prourokinase-like polypeptide.

Moreover, the present invention provides a plasmid containing the above-mentioned DNA segment, control regions for expression thereof, and a DNA sequence necessary for reproduction in *E. coli*.

Still further, the present invention provides *E. coli* transformed with the plasmid.

The present invention also provides a process for the production of human prourokinase-like polypeptide, characterized by culturing the above-mentioned transformed E. coli and recovering the polypeptide from the culture broth.

The present invention further provides a pharmaceutical preparation comprising the above-mentioned human prourokinase-like polypeptide together with a pharmaceutical excipient.

The present invention also encompasses the use of the above-mentioned human prourokinase-like polypeptide for the production of a thrombolytic preparation.

The present invention also provides a prophylactic or therapeutic method against thrombus formation, characterized by administering the above-mentioned human prourolinase to a patient.

The present rapidly acting human prourokinase, not only are activated by plasimin, but also are rapidly activated by thrombin produced only at a time of thrombus formation, while natural type human prourokinase does not have the latter property. Therefore, when the present prourokinase-like polypeptides are administered, an expression of the activity thereof is limited to sites at which thrombus is present, in comparison to the conventional human prourokinase, and occurs rapidly at an early stage of the thrombus formation, and therefore, are promising as a rapidly acting thrombolytic agent with less side effects such as systemic hemorrhage.

Further, where the gene containing a DNA segment coding for the present human prourokinase-like polypeptide is used, the polypeptide is efficiently expressed, and therefore, the polypeptide can be economically produced.

BRIEF DESCRIPTION OF THE DRAWINGS

FIGS. 1-1 to 1-4 represent a nucleotide sequence of cDNA coding for a natural type human prourokinase and a corresponding amino acid sequence;

FIGS. 2-1 and 2-2 represent the construction of an intermediate plasmid pMUT9Q from starting plasmids pMUT4L and pMUP1pm;

FIG. 3 represents the construction of plasmid pIO-1 from plasmid pMUT9Q;

FIG. 4-1 represents nucleotide sequences of synthetic DNA oligomers coding for mutated amino acids at the 156th, 157th and 158th positions in human prourokinase-like polypeptides of the present invention, and corresponding amino acid sequences;

FIGS. 4-2 and 4-3 represent nucleotide sequences of further similar synthetic DNA oligomers and corresponding amino acid sequences;

FIG. 8 represents a process for the construction of

Figure 9:
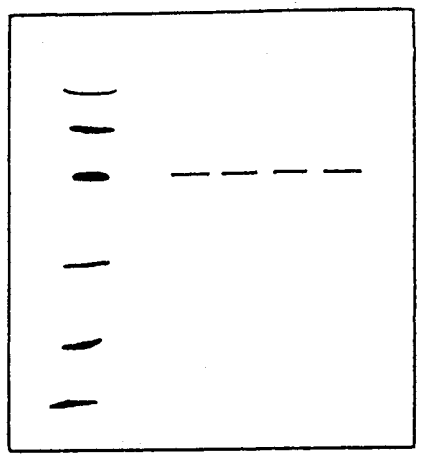
FIG. 9 represents an SDS-polyacrylamide gel electrophoresis pattern for purified preparation of the present mutant prourokinases Q-RPK and Q-RPR.

Note, the results obtained when natural type prourokinase and a mutant prourokinase Q(135) D(157) are used as control preparation are also shown in FIGS. 9

BEST MODE OF CARRYING OUT THE INVENTION

A. Rapidly acting human prourokinase-like polypeptide

The present rapidly acting human prourekinase-like polypeptide has the following amino acid sequence:

$$(Met)\text{-}Ser^1 - X^{156}.Y^{157}.Z^{158}\text{---}$$

wherein Met is an occasionally present methionine, Ser is the first N-terminal serine, X is the 156th arginine or other amino acid, Y is the 157th proline, glycine, alanine or valine, Z is the 158th lysine or arginine, and the solid lines are the same amino acid sequences as corresponding parts of an amino acid sequence of a natural type human prourokinase or a human prourokinase-like polypeptide wherein the 135th lysine is changed to an amino acid other than a basic amino acid, or has substantially the same amino acid sequence as the above-mentioned amino acid sequence.

Human prourokinase is a polypeptide consisting of 411 amino acids, and the amino acid sequence thereof is already known (literature 3). The plasminogen activator activity of human prourokinase is low, and it is considered that the activity thereof is exhibited in vivo by cleavage of a peptide bond between the 158th lysine and the 159th isoleucine (literature 3), usually by plasmin. In a normal organism, plasmin is present as plasminogen, which is an inactive precursor, but once thrombus has been formed by a pathogenic cause, the vascular wall and the like is stimulated to secrete the tissue plasminogen activator which then generates plasmin on a thrombus surface, and the plasmin triggers the onset of thrombolysis (literature 1). Therefore, when prourokinase is administered to an organism, an expression of the activity thereof is limited to a site at which plasmin is present, i.e., thrombus surface, resulting in a prevention of the tendency to systemic hemorrhage found when human urokinase is administered. Where prourokinase is used as thrombolytic agent, however, a small application amount does not produce a sufficient amount of plasmin, and therefore, the thrombus cannot be efficiently lyzed, but in the case of an excess application amount, even though a large amount of plasmin is temporarily produced, an increased amount of the plasmin does not increase the thrombolysis due to the distance thereof from a thrombus site, resulting in a decreased thrombolysis efficiency. Moreover, a portion of plasmin thus produced is inactivated by inhibitors such as α2-antiplasmin, and another portion activates prourokinase at a site at which thrombus is not present, resulting in side effects such systemic hemorrhage. Therefore, in the administration of prourokinase, the dose and manner of administration which do not produce a temporarily excess amount of plasmin is desired. Moreover, it is reported that prourokinase, when cleaved at a peptide bond between Arg 156 and Phe 157, is no longer activated by plasmin (literature 2).

Thrombin converts fibrinogen to fibrin monomer at a final stage in a blood coagulation cascade, and the fibrin monomers self-associate to form a large fibrin network which forms thrombus. On the other hand, although a portion of the thrombin is captured in the fibrin network during the above-mentioned process, another portion of the thrombin is released to the thrombus surface, and acts to expand the network.

After the formation of thrombus, although the thrombus which escaped capture is rapidly inactivated by antithrombin III or the like, the captured thrombin is diffused and appears on the thrombus surface (literatures 4 and 5) while maintaining the activity thereof. Moreover, since the captured thrombin is released when the thrombus is dissolved by fibrolytic enzyme (literature 4), a reformation of the thrombus occurs.

The present inventors created by replacement of the 157th phenylalanine with proline, completely novel prourekinase having the following properties:
  i) the rate of activation by plasmin is lower than that of natural type prourokinase; and
  ii) it is activated by thrombin, in contrast with natural type prourokinase which is not activated by thrombin.

Due to the property i), the present prourokinase is expected not to exhibit side effects such as systemic hemorrhage even if administered in a large amount. Moreover, taking into account the above-mentioned localization of thrombin, due to the property ii), it is expected that the present prourokinase will not only rapidly and thrombus-site-specifically exhibit the activity thereof from an early stage of thrombus formation to termination thereof, but also will exhibits an effective lytic activity when thrombus is reformed by thrombin released after thrombolysis.

Note, the above-mentioned facts originally found by the present inventors relating to prourokinase are reasonably explained according to the substrate specificity of thrombin (literature 6). Namely, in the following amino acid sequence:

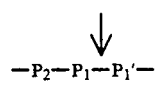

$$-P_2-P_1-P_1'-$$

wherein $P_2$, $P_1$ and $P_1'$ represent any amino acid, and the symbol ↓ represents a cleavage site for thrombin, where $P_1$ is lysine or arginine, and $P_2$ is proline, glycine, alanine or valine, thrombin cleaves a peptide bond between $P_1$ and $P_1'$, with a proviso that when $P_1$, is proline the cleavage does not occur. Accordingly, the response of natural type prourokinase to thrombin where the 157th amino acid is phenylalanine and of a prourokinase wherein the 157th amino acid has been replaced with proline, is summarized as follows:

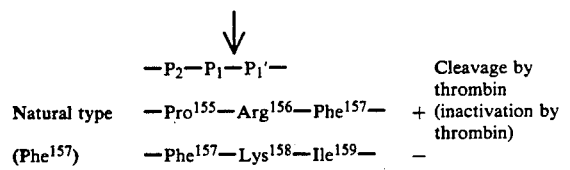

|  |  | Cleavage by thrombin |
|---|---|---|
| Natural type (Phe$^{157}$) | $-Pro^{155}-Arg^{156}-Phe^{157}-$ | + (inactivation by thrombin) |
|  | $-Phe^{157}-Lys^{158}-Ile^{159}-$ | − |
| Present invention (Pro$^{157}$) | $-Pro^{155}-Arg^{156}-Pro^{157}-$ | − |
|  | $-Pro^{157}-Lys^{158}-Ile^{159}-$ | + (activation by thrombin) |

Namely, for natural type prourokinase, first in a sequence of the 155th proline, the 156th arginine and the 157th phenylalanine, a peptide bond between the 156th arginine and the 157th phenyl alanine is easily cleaved by thrombin, and therefore, the natural type prourokinase is inactivated, while in a sequence of the 157th phenylalanine, the 158th lysine and the 159th isoleucine, it is difficult for thrombin to cleave a peptide bond between the 158th lysine and the 159th isoleucine, and therefore the natural type prourokinase is not activated by thrombin On the other hand, for the present prourokinase wherein the 157th amino acid is proline, first in a sequence of the 155th proline, the 156th arginine and the 157th proline, a peptide bond between the 156th arginine and the 157th proline is not cleaved by thrombin, and therefore, the present prourokinase is not inactivated, while in a sequence of the 157th proline, the 158th lysine and the 159th isoleucine, a peptide bond between the 158th lysine and the 159th isoleucine is easily cleaved by thrombin, and therefore, the present prourokinase is activated.

Further, the reason why the prourokinase, wherein the 157th amino acid has been replaced with proline, was activated also by plasmin can be explained as follows. Since the 157th site is easily affected by plasmin because this site is originally a cleavage site for plasmin, the plasmin cleavage action is not largely affected by the replacement of the 157th amino acid.

According to the present invention, taking an account the above-mentioned substrate specificity of thrombin, as embodiments of combinations of the above-mentioned X, Y and Z, the following polypeptides were prepared.

| Symbol | X | Y | Z |
|---|---|---|---|
| (1) RPK | Arg | Pro | Lys |
| (2) RPR | Arg | Pro | Arg |
| (3) QPR | Gln | Pro | Arg |
| (4) SGR | Ser | Gly | Arg |

As described hereinafter in detail, the effect of plasmin and thrombin on the activation of the abovementioned various polypeptides was tested, and as a result, all the above-mentioned four combinations of the replacements were confirmed to provide these novel prourokinases with desired properties, i.e., the property of being activated by plasmin and thrombin as well as the property of not being inactivated by thrombin. Moreover, as described hereinafter in detail, the effect of thrombin on the lysis time of a fibrin clot was determined, and as a result, all the above-mentioned four combinations of the replacements were confirmed to provide the prourokinases with the desired property; i.e., the higher the thrombin concentration, the faster the fibrin clot is dissolved. Accordingly, in view of the above it can be reasonably expected that polypeptides defined by all the combination of the definitions of X, Y and Z have the following properties; they are activated by plasmin and thrombin; they are not inactivated by thrombin; and the higher the thrombin concentration, the faster they dissolve the fibrin clot. Therefore, all the prourokinase-like polypeptides defined by the above-mentioned combinations of the definitions X, Y and Z are within the scope of the present invention.

As combinations of X, Y and Z of the present invention, in addition to the above-mentioned combinations (1) RPK, (2) RPR, (3) QPR, and (4) SGR, for example, the following combinations can be used:

| (5) X-Gly-Lys | (TUK-XGK) |
|---|---|
| (6) X-Ala-Lys | (TUK-XAK) |
| (7) X-Ala-Arg | (TUK-XAR) |
| (8) X-Val-Lys | (TUK-XVK) |
| (9) X-Val-Arg | (TUK-XVR) | wherein X represents Arg present in a natural polypeptide or any other amino acid.

In the above-mentioned general formula, amino acid sequences represented by solid lines are the same as corresponding parts of an amino acid sequence of natural type human prourokinase or of human prouro- kinase-like polypeptides wherein the 135th lysine has been replaced by an amino acid other than a basic amino acid. As an amino acid sequence of the natural type human prourokinase, there can be mentioned an amino acid sequence consisting of 411 amino acids encoded by cDNA corresponding to mRNA derived from a human kidney This amino acid sequence is set forth in FIGS. 1-1 to 1-3 by amino acid symbols composed of three capitalized alphabetical characters.

The human prourokinase-like polypeptide wherein the 135th lysine has been replaced by an amino acid other than the basic amino acid is described in detail in Japanese Patent Application No. 61-12984 (Japanese Unexamined Patent Publication No. 62-143686) (EP 0210279). As amino acids other than the basic amino acid for the 135th position, alanine, asparagine, aspartic acid, glutamine, glutamic acid, phenylalanine, glycine, isoleucine, leucine, methionine, serine, threonine, valine, tryptophan, tyrosine, proline and the like can be mentioned In the above-mentioned general formula, (Met) represents methionine occasionally present adjacent to the N-terminal first Ser of prourokinase.

The rapidly acting human prourokinase-like polypeptide of the present invention, in addition to the polypeptides comprising the above-mentioned amino acid sequences, includes polypeptides having essentially the same amino acid sequence as disclosed above. The term, essentially the same amino acid sequence, herein means those amino acid sequences wherein one or a few amino acids other than X, Y and Z in the above-mentioned amino acid sequence are replaced by other amino acid(s) or deleted, or one or a few amino acids are added to the above-mentioned amino acid sequence, but the physiological properties of prourokinase and the properties characteristic to the present invention are still maintained; i.e., easily activated by plasmin and thrombin. It is well known to a person with ordinary skill in the art that, in some cases, the change of an amino acid sequence in a peptide having a particular physiological activity in a region not relating to the physiological activity does not affect the physiological activity. Therefore, polypeptides containing the above-mentioned changes are within the scope of the present invention so long as they have the characteristics of the present invention.

B. Genes system for human prourokinase and process for production thereof

The present invention also relates to a gene system useful for the production of rapidly acting human prourokinase and a process for the production of the human prourokinase using that gene system. The gene system herein includes DNA segments coding for a desired human prourokinase-like polypeptide, expression plasmids containing the DNA segment, and a host to which the expression plasmid has been introduced.

A DNA segment coding for a rapidly acting human prourokinase of the present invention is derived from a DNA coding for a natural human prourokinase, or a DNA coding for a stabilized human prourokinase-like polypeptide described in Japanese Patent Application No. 61-12984 (EP 0210279). Namely, in these DNA's, codons coding for amino acids corresponding to the target amino acids (the above-mentioned X, Y and Z) are mutated to convert these codons to codons coding for desired amino acids. The mutation is introduced by replacing a DNA fragment containing a codon(s) coding for the target amino acid(s) with a synthetic DNA fragment wherein a coden(s) coding for the target amino acid(s) is changed to a codon(s) coding for the desired amino acid(s). The DNA fragment to be replaced is preferably a relatively small fragment generated by appropriate restriction enzyme(s). For the synthetic DNA fragment, as codons for the target amino acids and other amino acids, all codons in the degeneration, preferably codons easily expressed in a host, are used and are selected so that a sequence of the codons does not form a folding structure at the mRNA level. Alternatively, well known M13 phages can be used to introduce the mutation.

Note, in an embodiment of the present invention, as a gene source coding for prourokinase, plasmid pMUT4L and plasmid pMUPlpm are used. The process for the production and characterization of these plasmids is described in detail in Japanese Patent Application No. 61-12984 (Japanese Unexamined Patent Publication No. 62-143686) (EP 0210279). Although the plasmid pMUT4L contains a DNA fragment coding for amino acids of a natural prourokinase, for improvement of the expression, in the N-terminal coding region thereof, the following codons are used in place of codons in native cDNA.

```
Met Ser Asn Glu Leu His Gln Val Pro Ser
5'ATG AGC AAC GAG CTC CAC CAG GTT CCG TCG 3'
3'TAC TCG TTG CTC GAG GTG GTC CAA GGC AGC 5'
```

Note, a process for the construction of pMUT4L is set forth in Reference Examples 1 and 2.

A DNA segment coding for the present rapidly acting human prourokinase is recombinated to form an expression plasmid. The expression plasmid is introduced into host cells to accumulate a desired human prourokinase in the host cells or a culture broth. A process for the production of human prourokinase, described in Japanese Patent Application No. 61-12984 (Japanese Unexamined Patent Publication No. 62-143686) (EP 0210279) totally applies to the production of the rapidly acting human prourokinases of the present invention. Although a definite embodiment of the process is set forth herein in the Examples, hosts and expression vectors other than those described to the Examples also are within the scope of the present invention.

Where E. coli cells are used as host cells, the produced prourokinase-like polypeptide is usually recovered as an insoluble pellet after disruption of the cells by ultrasonication or a Gaulin homogenizer. After the pellet is dissolved in 4 M guanidine hydrochloride aqueous solution, a steric structure of the desired product is restored by a reaction thereof with a thiol compound or an oxidation thereof in air in the presence of guanidine hydrochloride. Next, after recovery of the desired product by salting out, using, for example, ammonium sulfate, the product is purified by chromatography using a hydrophobic interaction in the presence of guanidine hydrochloride or chromatography using an interaction with metal ions, although other conventional biochemical separation techniques can be used.

The present human prourokinase-like polypeptides are useful as a prophylactic or therapeutic agent, especially a therapeutic agent used against the thrombus formation, and accordingly, are administered parentally, for example, intravenously, intraperitoneally, subcutaneously or intramuscularly. The application dosage depends on the condition of a patient and manner of application and the like. Pharmaceutical preparations for parenteral application are usually in the form of a solution in a conventional injectable excipient, or a lyophilized preparation obtained from such a solution.

Next, the present invention will be further definitely illustrated by, but is by no means limited to, the following Examples and Reference Examples Note, the reaction conditions used in the Examples are as follows.

Reaction of each restriction enzyme 10 units of a restriction enzyme was added to 50 μl of the following reaction mixture containing 1 μg of DNA (plasmid or DNA fragment), and the mixture was incubated at the following temperatures. Where partial digestion was carried out, 1 to 2 units of a restriction enzyme were added, and the incubation time was 0.5 to 1 hour.

| Restriction enzyme | Composition of reaction mixture | Reaction temperature |
| --- | --- | --- |
| Aat II | 10 mM Tris-HCl (pH 7.5), 50 mM KCl, 10 mM $MgCl_2$, 1 mM dithiothreitol | 37° C. |
| BamH I | 6 mM Tris-HCl (pH 7.9), 150 mM NaCl, 6 mM $MgCl_2$ | 30° C. |
| Ban II | 6 mM Tris-HCl (pH 7.4), 50 mM NaCl, 6 mM $MgCl_2$, 10 mM β-mercaptoethanol | 37° C. |
| Dra II | 10 mM Tris-HCl (pH 8.0), 40 mM KCl, 7 mM $MgCl_2$, 7 mM β-mercaptoethanol | 37° C. |
| EcoR I | 100 mM Tris-HCl (pH 7.5), 50 mM NaCl, 5 mM ($MgCl_2$) | 37° C. |
| Hind III | 10 mM Tris-HCl (pH 7.5), 60 mM NaCl, 7 mM $MgCl_2$ | 37° C. |
| Nar I | 6 mM Tris-HCl (pH 7.4), 6 mM $MgCl_2$, 6 mM β-mercaptoethanol | 37° C. |
| Pst I | 10 mM Tris-HCl (pH 7.5), 100 mM NaCl, 10 mM $MgCl_2$ | 37° C. |
| Sca I | 6 mM Tris-HCl (pH 7.4), 100 mM NaCl, 6 mM $MgCl_2$, 1 mM dithiothreitol | 37° C. |
| Sma I | 6 mM Tris-HCl (pH 8.0) 20 mM KCl, 6 mM $MgCl_2$, 6 mM β-mercaptoethanol | 25° C. |

Reaction for Blunt End Formation of DNA by $T_4$ DNA Polymerase

A 0.5 to 1 unit of $T_4$ DNA polymerase was added to 50 μl of the following reaction mixture containing 1 to 2μg of a linear DNA, and the mixture was incubated at 37° C. for one hour.

Composition of reaction mixture 67 mM Tris-HCl (pH 8.8), 6.7 mM $MgCl_2$, 16.6 mM $(NH_4)_2SO_4$, 10 mM β-mercaptoethanol, 6.7 μM ethylenediaminetetraacetic acid, 0.0167% bovine serum albumin, 330 μM dCTP, 330 μM dATP, 330 μM dGTP and 330 μM dTTP.

Reaction for Blunt End Formation of DNA by Klenow Fragment

A 0.5 to 1 unit of Klenow fragment was added to 50 μl of the following reaction mixture containing 1 to 2 μg of a linear DNA, and the mixture was incubated at 25° C. for one hour.

Reaction mixture 67 mM potassium phosphate buffer (pH 7.4), 6.7 mM MgC12 , 1 mM β-mercaptoethanol, 33 μM dATP, 33 μM 7 dTTP, 33 μM dGTP and 33 μM dCTP.

Reaction for Joining DNAs by $T_4$ DNA Ligase

To 7.5 μl of a DNA solution containing DNA fragments (about 0.1 μg) to be joined, were added 60 μl of A solution of "DNA ligation kit" from Takara Shuzo K.K. and 7.5 μl of B solution containing T4 DNA ligase, and the whole was mixed and incubated at 16° C. for 30 minutes.

Figures 1, 2:
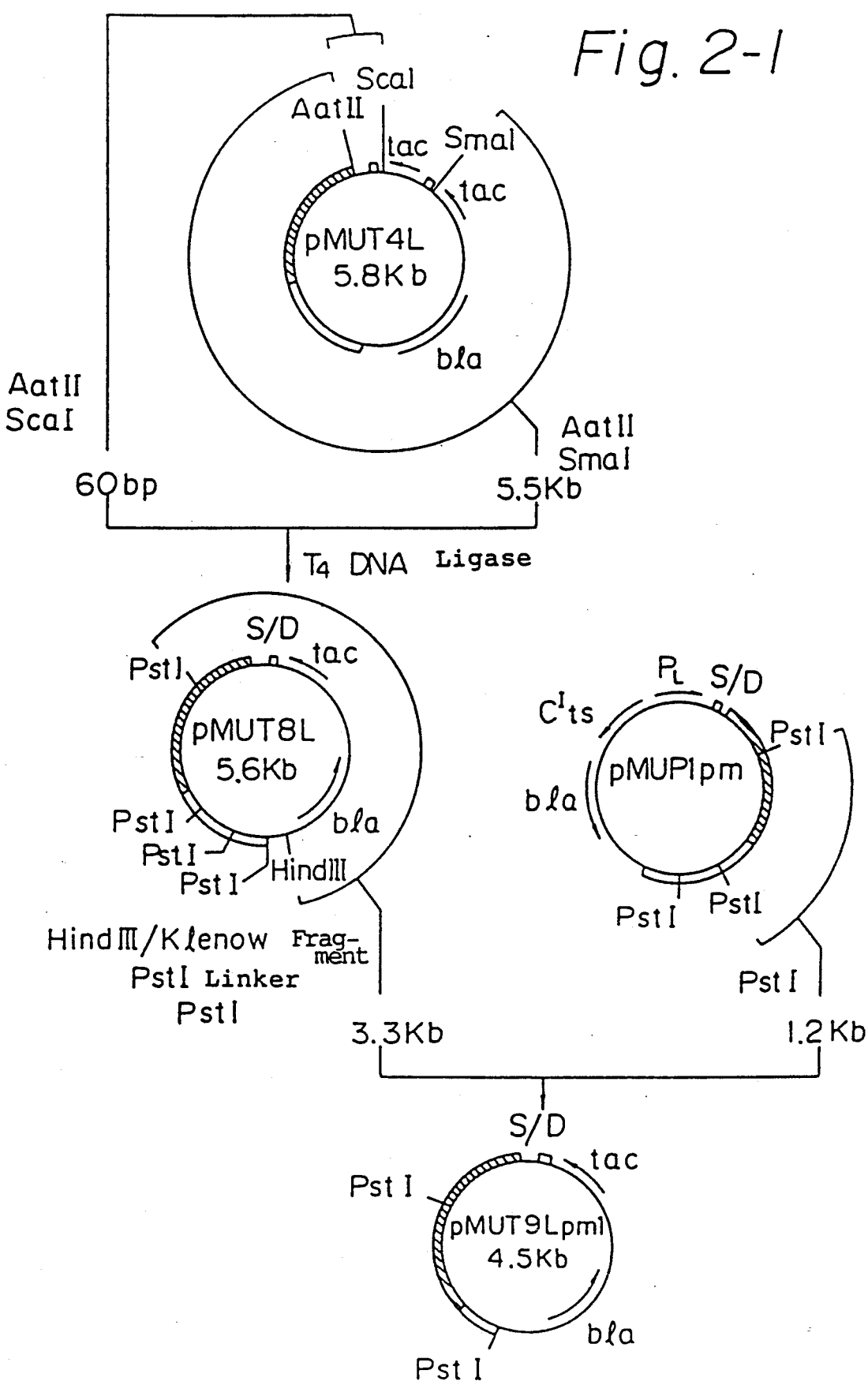
Figure 2:
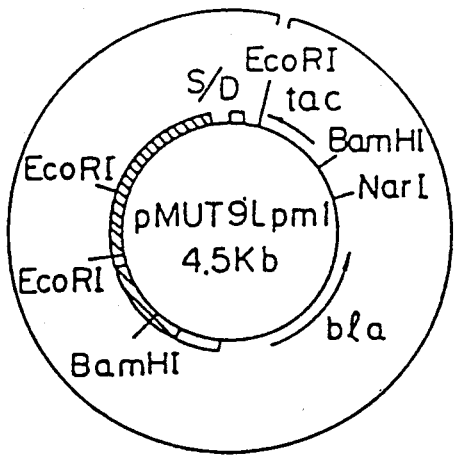
Figure 2:
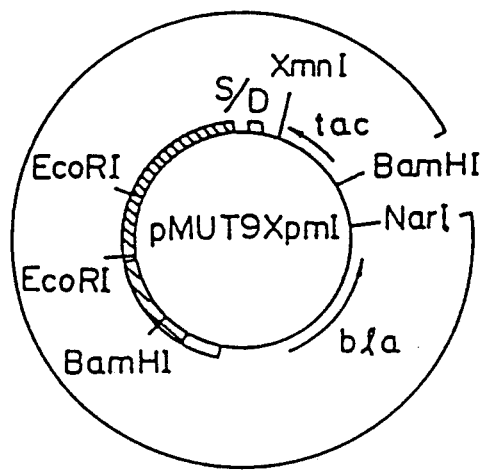
Figure 2:
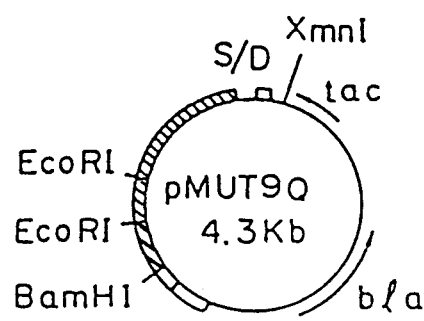

Example 1 Construction of Expression Plasmid FIGS. 2-1 and 2-2

(FIGS. 2-1 and 2-2)

Plasmid pMUT4L having two pairs of tac promoter/operator for expression of prourokinase was digested with restriction endonucleases AatII and SmaI, and a DNA fraction of about 5.5 kb was isolated by electroelution. On the other hand, the plasmid pMUT4L was digested with restriction endonucleases AatII and ScaI, and a DNA fragment of about 60 bp was isolated by electroelution. These two DNA fragments were ligated using T$_4$ DNA ligase, and E. coli was transformed. The transformant was analyzed by a rapid isolation method according to an alkaline lysis method, and plasmid pMUT8L having a pair of a tac promoter/operator was obtained.

Next, the pMUT8L was digested with restriction endonuclease HindIII, blunt-ended using a Klenow fragment, and after ligation with a commercially available PstI linker, digested with PstI. From the resulting digestion product, a 3.3 Kb DNA fragment was isolated by electroelution. On the other hand, plasmid pMUPlpm having a PL promoter and a gene for prourokinase wherein the 135th lysine has been converted to glutamine, was digested with a restriction enzyme PstI, and 1.2 kb DNA fragment was isolated by electroelution. These two DNA fragments were ligated by T$_4$ DNA ligase to obtain an expression plasmid pMUT9Lpml having a gene for prourokinase wherein the 135th lysine has been converted to glutamine, downstream of the tac promoter/operator.

Next, this plasmid pMUT9Lpml was partially digested with a restriction enzyme EcoRI, blunt-ended by a Klenow fragment, and self-circularized using a T$_4$ DNA ligase. From the resulting clones, a plasmid wherein only the EcoRI site present between a promoter/operator region and an S/D region has been converted to an XmnI site was selected, and designated pMUT9Xpml.

Next, the pMUT9Xpml was partially digested with restriction enzymes BamHI and NarI, blunt-ended by a Klenow fragment, and self-circularized using a T$_4$ DNA ligase. From the resulting clones, a plasmid lacking a DNA fragment of about 200 bp between the BamHI site and NarI site, present upstream of a promoter/operator region, was selected and designated pMUT9Q. The pMUT9Q is an expression plasmid having a DNA fragment coding for prourokinase Q(135) wherein the 135th lysine has been converted to glutamic acid, downstream of the tac promoter/operator. Note, the mutant prourokinase Q(135) is the same as a mutant prourokinase obtained from pMUP1pm.

Escherichia coli containing plasmid pMUPlpm used as a starting material in this Example was deposited with the Fermentation Research Institute, Agency of Industrial Science and Technology as FERM BP-969 on Jan. 11, 1985, as an international deposition under the Budapest Treaty.

Note, although as described above the present human prourokinase-like polypeptide encoded in the plasmid pMUT9Q has glutamine as the 135th amino acid, a plasmid corresponding to the plasmid pMUT9Q but coding for threonine as the 135th amino acid can be obtained in the same manner as described above by using, in place of the above-mentioned plasmid pMUPlpm, a plasmid pMUT4Lpm2 containing a DNA fragment coding for a human prouro-kinase-like polypeptide having threonine as the 135th amino acid.

Escherichia coli χ1776/pMUT4Lpm2 containing the above-mentioned plasmid pMUT4Lpm2 was deposited as FERM BP-970 on Apr. 18, 1985 as an international deposition.

Similarly, by using a plasmid pMUT4Lpm3 in place of the plasmid pMUPlpm, a plasmid corresponding to the above-mentioned plasmid pMUT9Q but coding for lysine as the 135th amino acid can be obtained Escherichia coli X1776/pMUT4Lpm3 containing the plasmid pMUT4Lpm3 was deposited as FERM BP-971 on Jul. 11, 1985, as an international deposition.

Example 2

Figure 3:
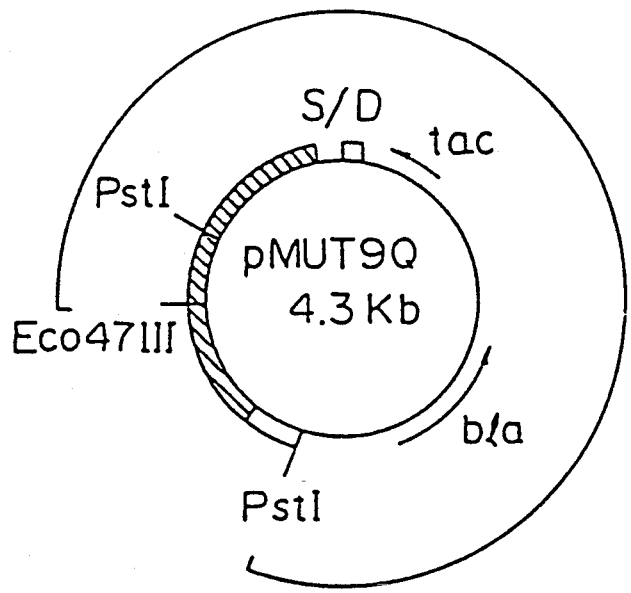
Figure 3:
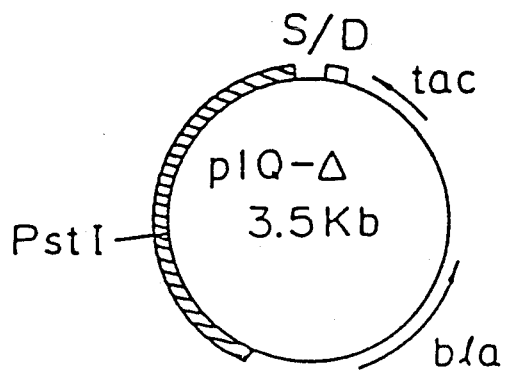

Construction of Plasmid pIQ-Δ for Introduction of Mutation (FIG. 3)

The plasmid pMUT9Q obtained in Example 1 was completely digested with an restriction enzyme Eco47III, and then partially digested with a restriction enzyme PstI. Next, after blunt end formation by T$_4$ DNA polymerase, the fragment was self-circularized using a T$_4$ DNA ligase. Among the resulting clones, a plasmid lacking only a Eco47III-PstI fragment of 0.77 kb was selected, and designated pIQ-Δ.

Similarly, a plasmid corresponding to the pIQ-Δ but coding for threonine or lysine as the 135th amino acid also can be obtained.

Example 3.

Figure 5:
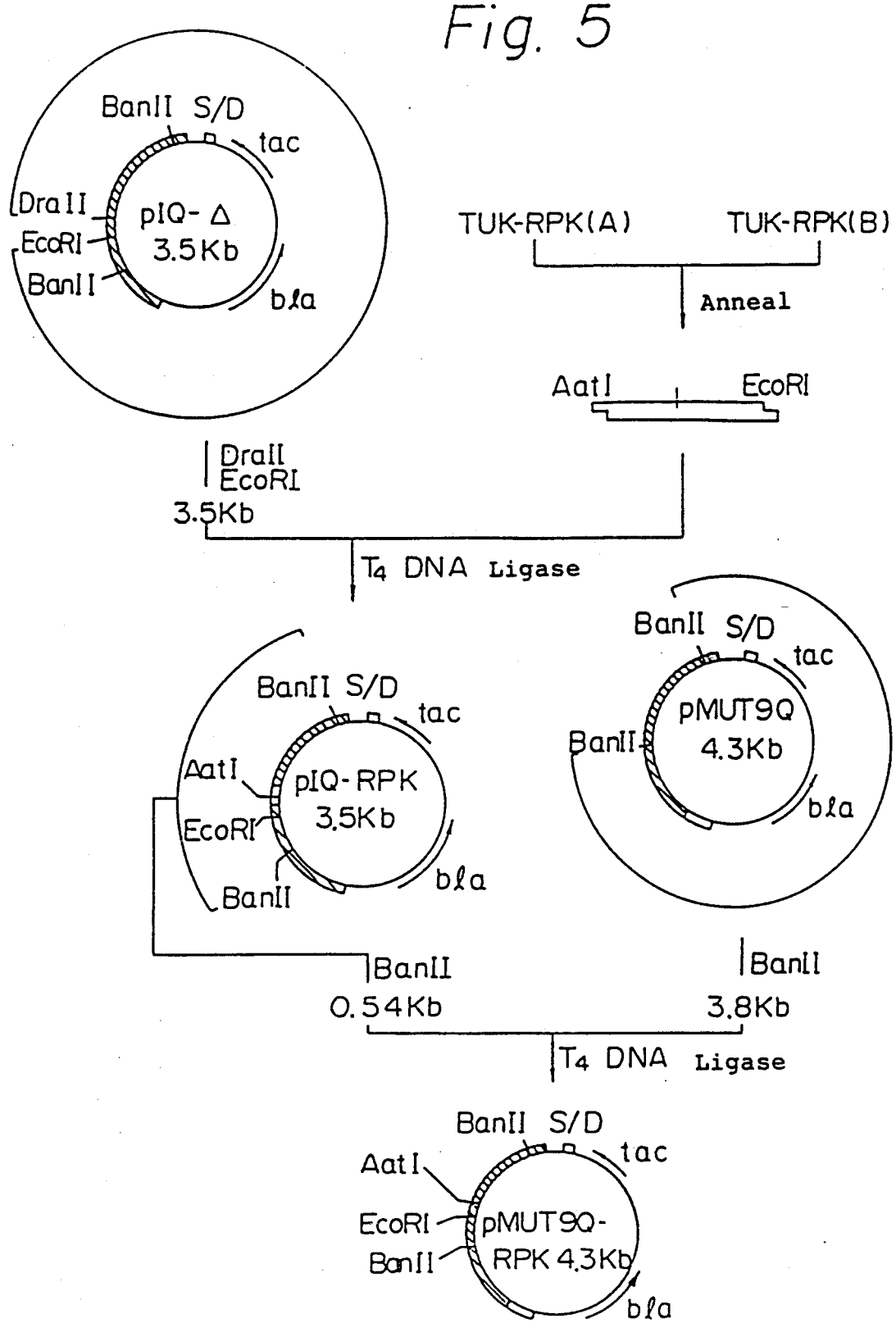
FIG. 5 represents a process for the construction of plasmid pMUT9Q-RPK.

Construction of Q-RPK Type Mutant FIG. 5)

The plasmid pIQ-Δ obtained in Example 2 was digested with DraII and EcoRI, and a 3.5 kb DNA fragment was isolated by electroelution. On the other hand, two oligonucleotides, TUK-RPK (A) and TUK-RPK (B) (FIG. 4-1), synthesized by a phosphite method were annealed, and ligated with the 3.5 kb DNA fragment using T$_4$ DNA ligase to obtain an intermediate plasmid pIQ-RPK. Next, the pIQ-RPK was digested with a restriction enzyme BanII, and a 0.54 kb DNA fragment was isolated by electroelution. On the other hand, the plasmid pMUT9Q obtained in Example 1 was digested with a restriction enzyme BanII, and a 3.8 kb DNA fragment was isolated by electroelution. These two DNA fragments were ligated using a T$_4$ DNA ligase to obtain a plasmid pMUT9Q-RPK. This plasmid is an expression plasmid containing a DNA sequence coding for a mutant type human prourokinase Q-RPK wherein the 157th phenylalanine has been converted to proline and the 135th lysine has been converted to glutamine, downstream of the tac promoter/operator.

Escherichia coli JM103 (pMUT9Q-RPK) containing this plasmid was deposited with Deutsche Sammulung von Microorganismen as DSM 4187, on Jul. 22, 1987 as an international deposition.

Example 4

Figure 6:
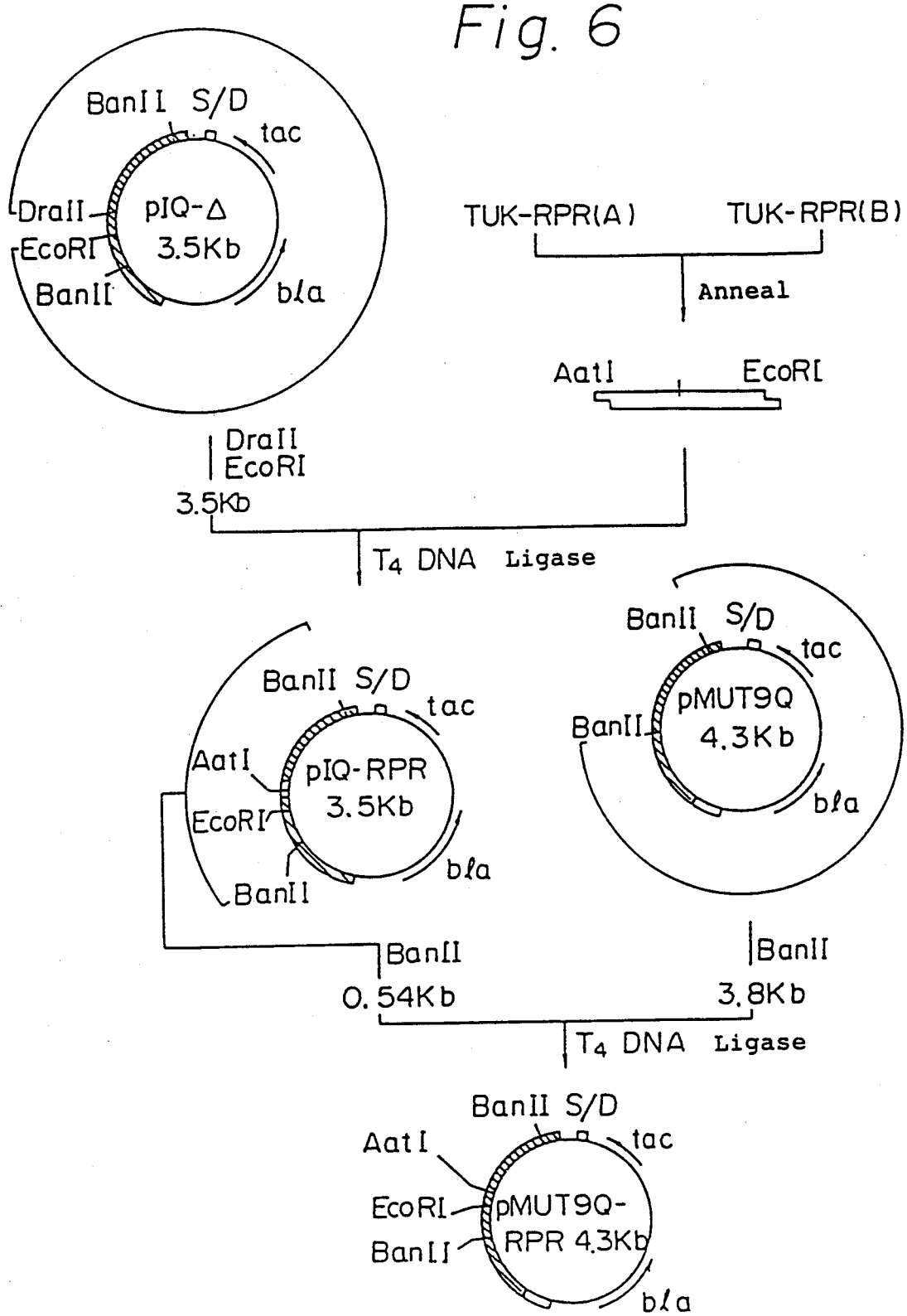
FIG. 6 represents a process for the construction of plasmid pMUT9Q-RPR.

Construction of Q-RPR Type Mutant (FIG. 6)

The plasmid pIQ-Δ obtained in Example 2 was digested with restriction enzymes DraII and EcoRI, and a 3.5 kb DNA fragment was isolated by electroelution. On the other hand, two oligomer TUK-RPR (A) and TUK-RPR (B) (FIG. 4-1) synthesized by a phosphite method were annealed and ligated with the 3.5 kb DNA fragment using a T$_4$ DNA ligase, to obtain an intermediate plasmid pIQ-RPR. Next, the pIQ-RPK was digested with a restriction enzyme BanII, and a 0.54 kb DNA fragment was isolated by electroelution. On the other hand, the plasmid pMUT9Q obtained in Example 1 was digested with a restriction enzyme BanII, and a 3.8 kb DNA fragment was isolated by electroelution. These two DNA fragments were ligated using T₄ DNA ligase to obtain a plasmid pMUT9Q-RPR This plasmid is an expression plasmid containing a DNA sequence coding for a mutant type human prourokinase Q-RPR wherein the 157th phenylalamine has been converted to proline, the 158th lysine has been converted to arginine, and the 135th lysine has been converted to glutamine, downstream of the tac promoter/ operator.

*Escherichia coli* JM103 (pMUT9Q-RPR) containing this plasmid was deposited with Deutsche Sammulung von Microorganismen as DSM 4186 on Jul. 22, 1987 as an international deposition.

Figure 7:
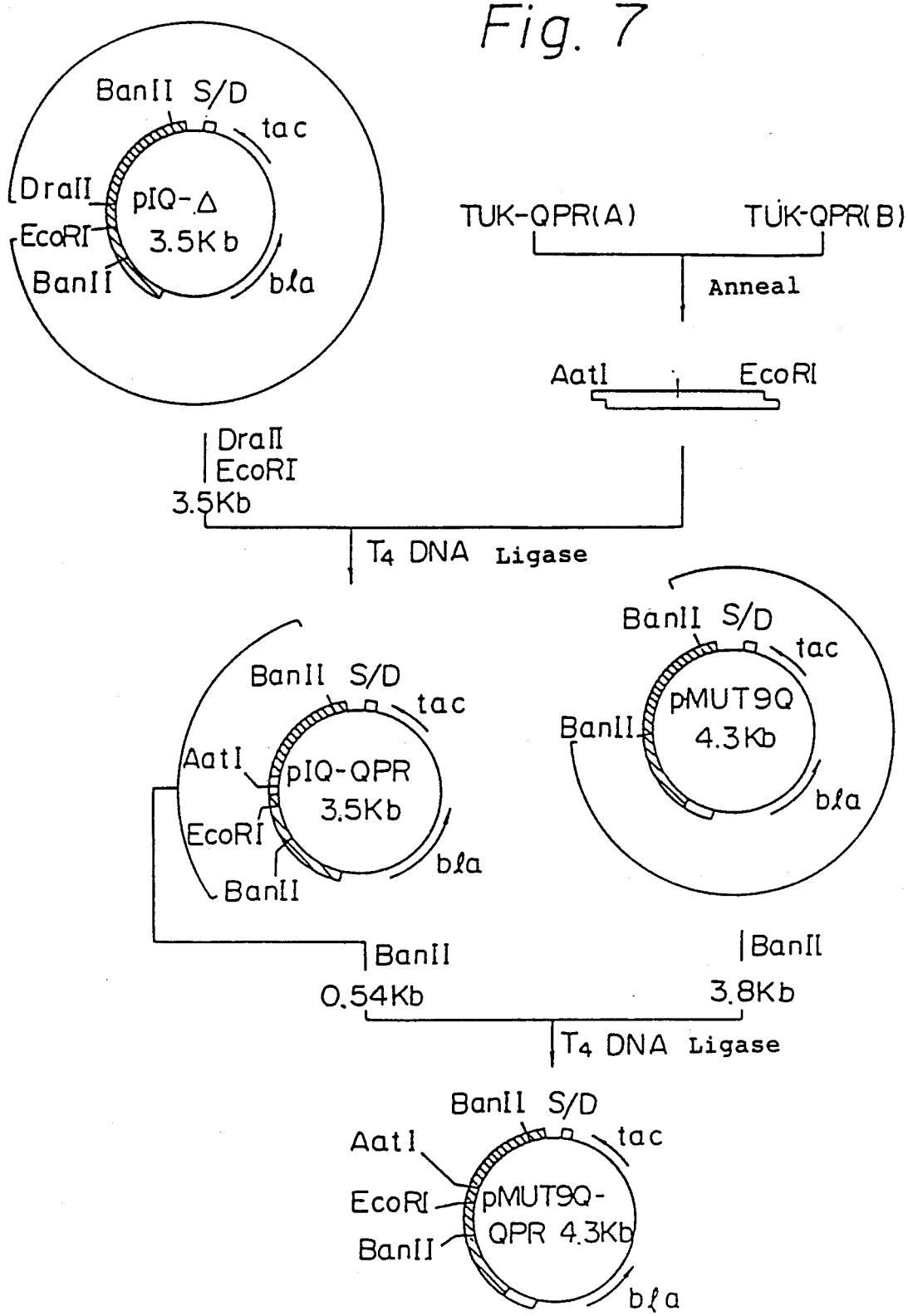
FIG. 7 represents a process for the construction of plasmid pMUT9Q-QPR.

Example 5 Construction of Q-QPR Type Mutant (FIG. 7)

The plasmid pIQ-Δ obtained in Example was digested with DraII and EcoRI, and a 3.5 kb DNA fragment was isolated by electroelution. On the other hand, two oligonucleotides, TUK-QPR (A) and TUK-QPR (B) (FIG. 4-1), synthesized by a phosphite method were annealed, and ligated with the 3.5 kb DNA fragment using T₄ DNA ligase to obtain an intermediate plasmid pIQ-QPR. Next, the pIQ-QPR was digested with a restriction enzyme BanII, and a 0.54 kb DNA fragment was isolated by electroelution. On the other hand, the plasmid pMUT9Q obtained in Example 1 was digested with a restriction enzyme BanII, and a 3.8 kb DNA fragment was isolated by electroelution. These two DNA fragments were ligated using a T₄ DNA ligase to obtain a plasmid pMUT9Q-QPR. This plasmid is an expression plasmid containing a DNA sequence coding for a mutant type human prourokinase Q-RPR wherein the 156th arginine has been converted to glutamine, the 157th phenylalamine has been converted to proline, the 158th lysine has been converted to arginine and the 135th lysine has been converted to glutamine, downstream of the tac promoter/operator.

*Escherichia coli* JMI03 (pMUT9Q-QPR) containing this plasmid was deposited with Deutsche Sammulung von Microorganismen as DSM 4188 on Jul. 22, 1987 as an international deposition.

Figure 8:
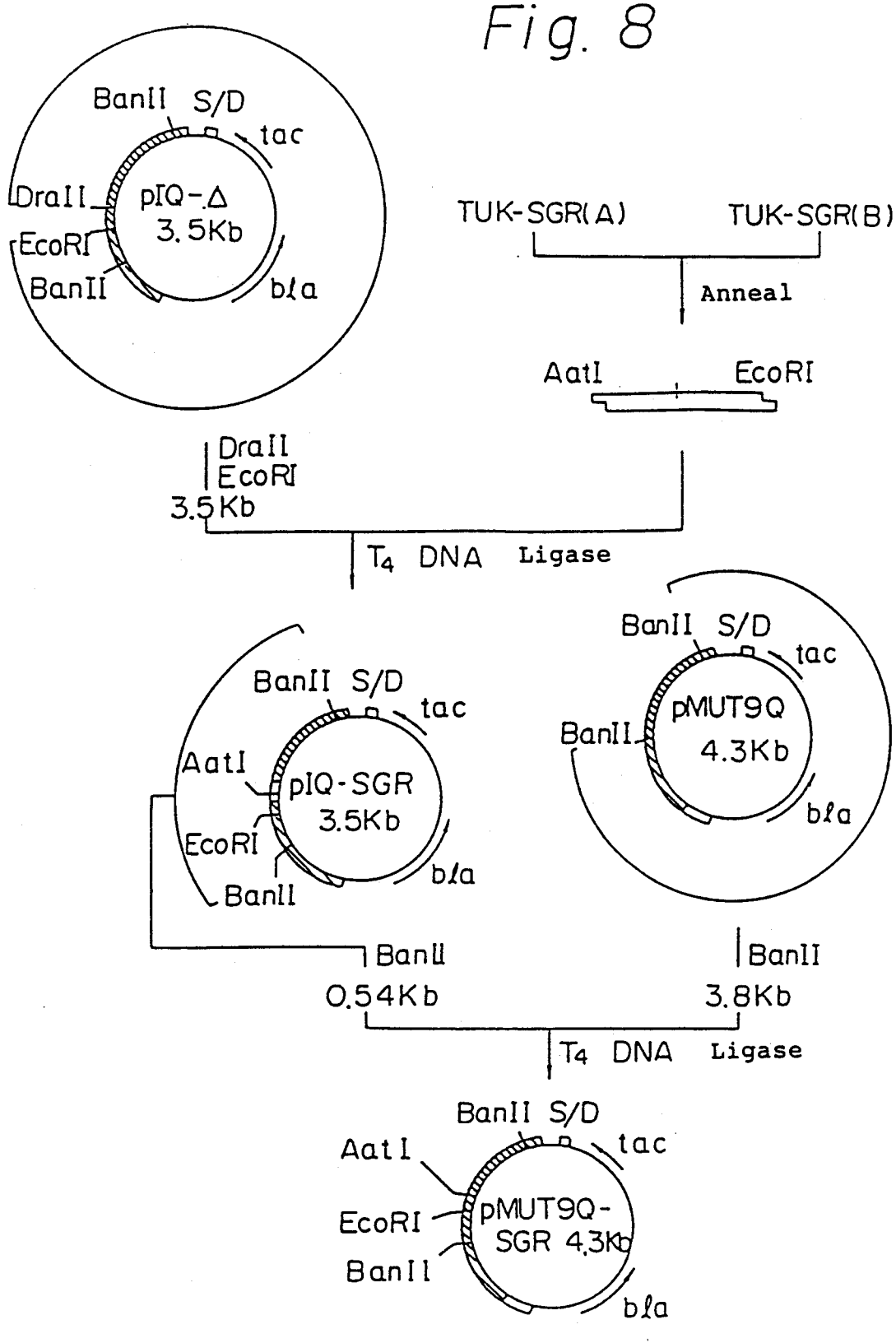

Example 6 Construction of Q-SGR Type Mutant (FIG. 8)

The plasmid pIQ-I obtained in Example 2 was digested with restriction enzymes DraII and EcoRI, and a 3.5 kb DNA fragment was isolated by electroelution. On the other hand, two oligomer TUK-SGR (A) and TUK-SGR (B) (FIG. 4-1) synthesized by a phosphite method were annealed and ligated with the 3.5 kb DNA fragment using a T₄ DNA ligase to obtain an intermediate plasmid pIQ-SGR.

Next, the pIQ-SGR was digested with a restriction enzyme BanII, and a 0.54 kb DNA fragment was isolated by electroelution.

On the other hand, the plasmid pMUT9Q obtained in Example 1 was digested with a restriction enzyme BanII, and a 3.8 kb DNA fragment was isolated by electroelution. These two DNA fragments were ligated using a T₄ DNA ligase to obtain a plasmid pMUT9Q-SGR. This plasmid is an expression plasmid containing a DNA sequence coding for a mutant type human prourokinase Q-SGR wherein the 157th phenylalamine has been converted to proline, the 158th lysine has been converted arginine, and the 135th lysine has been converted to glutamine, downstream of the tac promoter/operator.

*Escherichia coli* JM103 (pMUT9Q-SGR) containing this plasmid was deposited with Deutsche Sammulung von Microorganismen as DSM 4189 on July 22, 1987 as an international deposition.

Note, by using the same procedure as described in Examples 3 to 6, except for using a plasmid corresponding to the plasmid pIQ-I but coding for threonine or lysine as the 135th amino acid, plasmids coding for the present polypeptide wherein the 135th amino acid is threonine or lysine can be obtained.

Moreover, by using the same procedure as described above but using synthetic oligomers as set forth in FIG. 4-2, other mutants, for example, TUK-XGK, TUK-XAK, TUK-XAR, TUK-KVK and TUK-XVR, can be produced.

Example 7

Expression of Mutant Prourokinase Gene by *E. coli*

Plasmids pMUT9Q, pMUT9Q-RPK, pMUT9Q-RPR, and pMUT9Q-QPR obtained in Examples 1, 3, 4, and 5, respectively, were used to transform *E. coli* JM103 by a conventional procedure, and the resulting transformants were cultured in 5 ml of L-broth at 37° C. When the absorbance at 600 nm reached about 0.4 O.D, 50 μl of 100 mM isopropylthiogalactopyranoside (IPTG) was added, and culturing was continued for a further 4 hours to express each mutant prourokinase gene.

Example 8

Extraction of Gene Product from *E. coli*

Each culture broth obtained in Example 7 was centrifuged to recover cells corresponding to an amount of 7 O.D. ml, and these cells were then disrupted in 1.4 ml of 50 ml Tris-HCl (pH 8.0) buffer containing 0.1 M sodium chloride by ultrasonication to a turbidity extent of not more than 1 O.D at 600 nm, 0.8 ml of this disruptant solution was then centrifuged at 15 Krpm for 5 minutes, and the supernatant was discarded. The precipitate was suspended in 0.16 ml of a 50 mM Tris-HCl buffer containing 4 M guanidine hydrochloride, and the mixture was allowed to stand at a room temperature for 90 minutes to dissolve the precipitate. Next, 0.48 ml of a 50 mM Tris-HCl (pH 8.0) buffer containing 0.27 mM reduced glutathione and 1.33 mM EDTA was added, and the mixture was allowed to stand at 25° C. for 15 hours. Then solid ammonium sulfate was dissolved to 60% saturation to salt out a desired gene product, and to the salting out product was added an amount of Tris-HCl (pH 8.0) buffer containing 0.5 M sodium chloride, to prepare a crude extract of the gene product.

Example 9.

Properties of Gene Product Extracted from *E. coli* (1)

i) Measurement of urokinase activity by fibrin Plate Method

To 50 mM phosphate buffer (pH 7.4) containing 1% bovine fibrinogen, 0.25% agarose and 0.1 M sodium salt was added bovine thrombin to a final concentration of one unit/ml, to prepare a fibrin plate, on which 10 tl of a sample (prepared by appropriately diluting the crude extract prepared in Example 6) was then spotted, and after incubation at 37° C. for 16 hours, a diameter of a holo was measured and compared with that of a standard urokinase (Nippon Soda K.K.), to determine the activity. As a result, it was found that the urokinase activities of the crude extracts obtained in Example 8 were 370 IU/ml for a product from pMUTQ-RPK (Q-RPK), 380 IU/ml for a product from pMUT9Q-RPR (Q-RPR), and 360 IU/ml for a product from pMUT9Q-QPR (Q-QPR).

ii) Activation of Mutant Prourokinase by Plasmin

To 10 tl of a crude extract containing the mutant prourokinase Q-RPK, Q-RPR or Q-QPR was added 85 tl of 50 mM Tris-HCl (pH 8.0) containing 0.1 M NaCl and 0.01% Triton X-100, then to this mixture was added 5 tl of an aqueous solution of human plasmin (specific activity: 15 casein units/mg protein) to a final concentration of 0.1, 1, 10 or 50 tg/ml, and reaction was carried out at 37° C. for 15 minutes. The reaction was terminated by adding 5 tl of an aqueous solution containing hirudine in an amount of two fold that of thrombin (ratio of activities).

iv) Measurement of Activity of Activated Mutant Prourokinases using Synthetic Substrate S-2444

To 105 tl of Reaction Mixture Obtained in ii) and iii) was added 0.7 ml of 50 mM Tris-HCl (pH 8.0) buffer containing 0.2 mM S2444 (Daiichi Kagaku Yakuhin), 0.1 M sodium chloride and 0.1% Triton X-100, and reaction was carried out at 37° C for 30 minutes. The reaction was terminated by adding 0.1 ml of glacial acetic acid. Then an increase of an absorbance at 405 nm for 30 minutes of the reaction was measured, and an activity of the sample was calculated from a value for a standard urokinase (Nippon Soda K.K.) (increase of absorbance at 405 nm for 30 minutes is 0.0608 for one unit). The results are shown in Table 1, which shows that the mutant prourokinase Q-RPK, Q-RPR, and Q-QPR are activated by both plasmin and thrombin.

TABLE 1

| Mutant prourokinase | Activation of Various Mutant Prourokinase | | | | | | |
|---|---|---|---|---|---|---|---|
| | Plasmin (µg/ml) | | | | Thrombin (µg/ml) | | |
| | 0.1 | 1 | 10 | 50 | 0.1 | 1 | 10 |
| | (IU/ml) | | | | (IU/ml) | | |
| Q-RPK | 30.5 | 154 | 284 | 315 | 4.2 | 28.4 | 166 |
| Q-RPR | 15.8 | 121 | 272 | 315 | 75.8 | 385 | 428 |
| Q-QPR | 24.2 | 151 | 305 | 385 | 82.1 | 369 | 390 |
| Q (135) | 85.7 | 374 | 430 | 412 | 8.4 | 4.6 | 0 |

Example 10

Property of Gene Product Extracted from E. coli (2) (measurement of Lysis Time for Fibrin Clot First 0.2 ml of 50 mM phosphate buffer (pH 7.4) containing 15 mg/ml fibrinogen and 0.1 M sodium chloride was put into well of a 96-well microtiter plate, and after adding 0.03 ml of an aqueous solution containing 5 to 20 units/ml thrombin and 0.01 ml of the crude extract of Example 6 containing 165 IU/ml of mutant prourokinase, 0.06 ml of 50 mM phosphate buffer (pH 7.4) heated to 65° C. containing 0.75% agarose and 0.1 M sodium chloride was added and rapidly mixed (the time point was "0") and the mixture was incubated at 37° C. Although the mixture immediately gellated, it became transparent with an elapse of time. The time at which the gel started to become transparent and the time at which the gel became completely transparent were determined, and an intermediate time thereof was defined as a lysis time for a fibrin clot. The results are shown in Table 2.

TABLE 2

| | Time for Lysis of Fibrin Clot | | |
|---|---|---|---|
| | Thrombin (unit/ml) | | |
| Prourokinase | 0.5 | 1.0 | 2.0 |
| | (Min) | | |
| Q-RPK | 53 | 43 | 37 |
| Q-RPR | 36 | 30 | 24 |
| Q-QPR | 37 | 30 | 25 |
| Q (135) | 54 | 63 | 95 |
| Natural Prourokinase | 55 | 65 | 92 |

Table 2 shows that the present mutant prourokinases Q-RPK, Q-RPR, and Q-QPR rapidly lyse a fibrin clot in the presence of thrombin, in contrast to a natural type prourokinase and a mutant prourokinase Q(135) wherein the higher the concentration of thrombin, the longer the time necessary for the lysis of a fibrin clot. C.Y. Liu et al. shows that an activity of thrombin developing when the thrombus is formed in plasma reaches up to 15 units/ml, and this value is maintained for several minutes after a complete conversion of fibrinogen to fibrin (literature 4). From the above, it is considered that the present prourokinase is properly activated, at the beginning of thrombus formation, and exhibits a rapid thrombolytic action.

The present mutant polypeptides Q-RPK, Q-RPR, Q-QPR and Q-SGR are characterized by being activated by a cleavage between the 158th and 159th positions, and have an additional advantages in that they are not inactivated by a cleavage between the 156th and 157th positions.

Example 11

Purification of Mutant Prourokinase Q-RPK

The plasmid pMUT9Q-RPK obtained in Example 3 was used to transform E. coli JM103 by a conventional procedure. The transformant thus obtained was cultured in 1 l of L-broth at 37° C with shaking, and when an absorbance at 600 nm reached about 0.4, 10 ml of 0.1 M isopropyl-β-D-thiogalactopyranoside was added, followed by culturing for an additional four hours. Next, cells were recovered by centrifugation and disrupted by ultrasonication in 50 ml of 50 mM Tris-HCl (pH 8.0) buffer containing 0.1 M sodium chloride, until an absorbance at 600 nm became not more than 10. This disruptant solution was centrifuged at 15 Krpm for 30 minutes, and the supernatant was discarded. The precipitate was suspended in 50 mM Tris-HCl (pH 8.0) buffer containing 4 M guanidine hydrochloride, and the suspension was allowed to stand at a room temperature for 90 minutes to dissolve the precipitate.

Next, to the mixture was added 1500 ml of 50 mM Tris-HCl (pH 8.0) buffer containing 0.27 mM reduced glutathione and 1.33 mM ethylenediaminitetraacetic acid, and the mixture was allowed to stand at 25° C for 15 hours. The solid ammonium chloride was gradually dissolved in the mixture to 25% saturation at 4° C, and the mixture then centrifuged to eliminate any insoluble material. To the supernatant was added solid ammonium chloride to 50% concentration, to salt out a desired gene product (0-RPK), and the salting out product, was recovered by centrifugation and then dissolved in a mM Tris-HCl (pH 8.0) buffer containing ammonium sulfate of 7% saturation and 1 M guanidine hydrochloride. The solution was centrifuged to eliminate insoluble material, and the supernatant was applied to a column (φ1.5 cm×30 cm) of phenyl Sepharose CL-4B (Pharmacia LP Biochemicals) equilibrated with 50 mM Tris-HCl (pH 8.0) buffer containing ammonium sulfate of 7% saturation and 1 M guanidine hydrochloride. After washing the column with the equilibrating buffer, the desired gene product (Q-RPK) was eluted from the column using 50 mM Tris-HCl (pH 8.0) containing 1 M guanidine hydrochloride. Next, the elute was applied to a column (φ1.0 cm×30 cm) of zinc chelate Sepharose 6B equilibrated with 50 mM Tris-HCl (pH 8.0) buffer containing 0.5 M sodium chloride, and after washing the column with 150 ml of the equilibrating buffer, the desired gene product (Q-RPK) was eluted with 50 mM sodium acetate buffer (pH 5.4) containing 0.5 M sodium chloride. It was confirmed by SDS-polyacrylamide gel electrophoresis that the elute contained only a single protein. The results are shown in FIG. 9.

Example 12

Purification of Mutant Prourokinase Q-RPR

Using the plasmid pMUT9Q-RPR obtained in Example 4, and using the same procedure as in Example 11, the mutant prourokinase Q-RPR was purified. The purified preparation was confirmed to be a single protein by SDS-polyacrylamide gel electrophoresis. The results are shown in FIG. 9.

Example 13

Properties of Purified Mutant Prourokinases Q-RPK and Q-RPR (i) Activation by plasmin with elapse of time To 95 μl of 50 mM Tris-HCl (pH 8.0) buffer containing 0.01% Triton X-100, and 5 IU of purified mutant prourokinase Q-RPK or Q-RPR obtained in Example 11 or 12 was added 5 μl of plasmin aqueous solution containing $3 \times 10^4$ CU of plasmin, and reactions were carried out at 37° C. for different times. The reactions were terminated by adding 50 μl of aqueous solution containing 0.1 μg of soybean trypsin inhibitor. Next, the activity of mutant prourokinase contained in 105 μl of this reaction mixture was measured by the method described in (iv). Note, as a control, natural type urokinase and a purified preparation of mutant urokinase Q(135) P(157) (Japanese Unexamined Patent Publication No. 62-143686) (EP 0210279) were used. The results are shown in FIG. 10.

Figure 10:
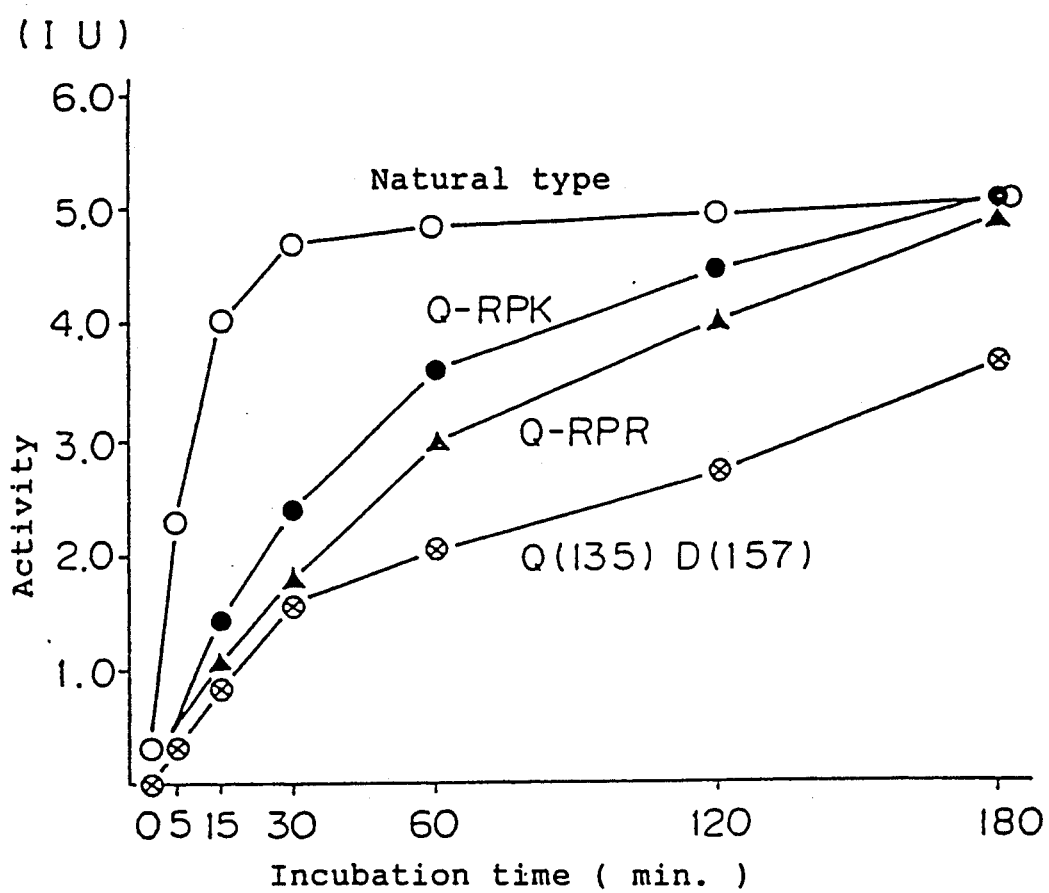
FIGS. 10 to 11 represent the progress of activation of purified preparation of the present mutant prourokinases Q-RPK and Q-RPR by plasmin or thrombin.

FIG. 10 shows that the mutant prourokinases Q-RPK and Q-RPR are activated by plasmin in the same way as the mutant prourokinase Q(135) D(157)

(ii) Activation by Thrombin with Elapse of Time

To 95 μl of 50 mM Tris-HCl (pH 8.2) buffer containing 0.01 Triton X-100, and 4 IU of a purified preparation of mutant prourokinase Q-RPK or Q-RPR, was added 5 μl of aqueous solution containing $4 \times 10^4$ NIH units of thrombin, and reactions were carried out for different times. Next, the activity of mutant prourokinase contained in 105 μl of this reaction mixture was measured by a method described in (iv). The reactions were terminated by adding 5 μl of aqueous solution containing $1 \times 10^3$ NIH units of hirudine. Note, as control samples, natural type prourokinase and a purified preparation of mutant prourokinase Q(135) D(157) were used. The results are shown in FIG. 11.

Figure 11:
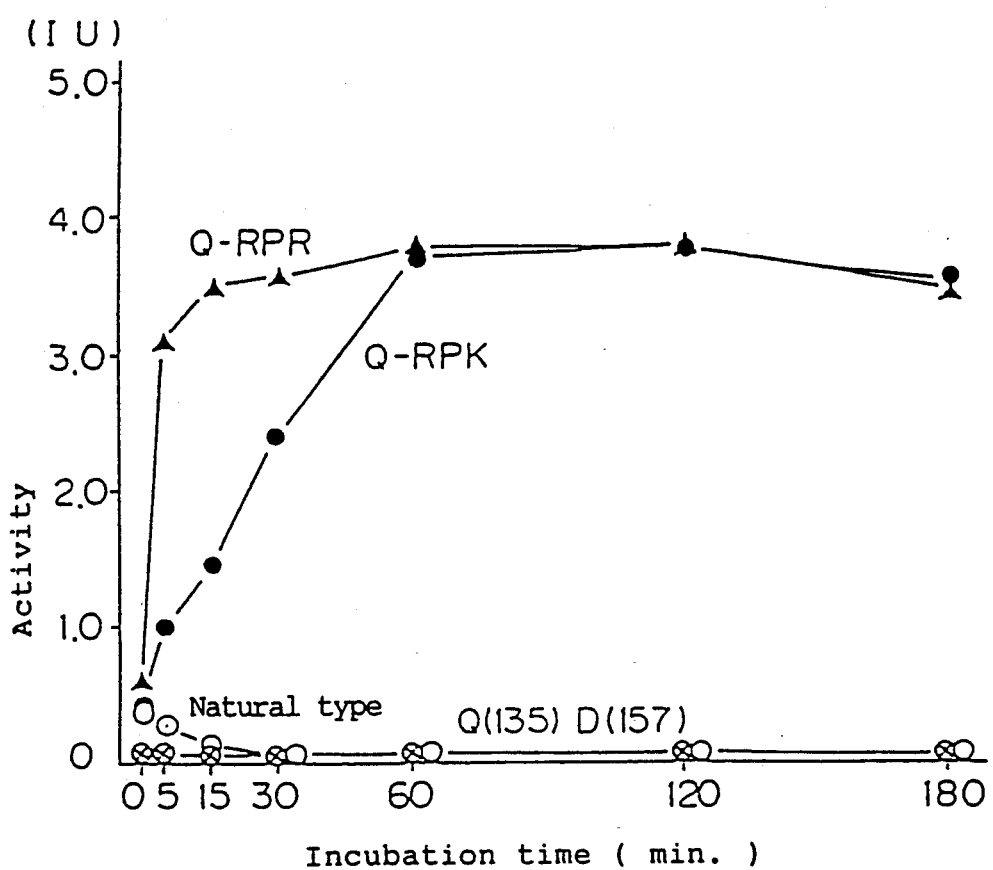

FIG. 11 shows that the mutant prourokinases Q-RPK and Q-RPR are rapidly activated by thrombin. This property is an absolutely new property not found in natural type prourokinase and mutant prourokinase Q(135) D(157).

(iii) Development of Residual Activity of Thrombin-Treated Preparation

To 85 μl of 50 mM Tris-HCl (pH 8.0) buffer containing 0.01 % Triton X-100, and mutant prourokinase Q-RPK or Q-RPR obtained in Example 11 or 12, 5 μl of an aqueous solution containing $4 \times 10^4$ NIH units of thrombin was added, and after reactions were carried out at 37° C. for different times, the reactions were terminated by adding 5 μl of an aqueous solution containing $1 \times 10^3$ NIH units of hirudine. Next, to the reaction mixture 5 μl of an aqueous solution containing 0.015 CU of plasmin was added, and after reaction was carried out at 37° C. for 30 minutes, the reaction was terminated by adding 5 μl of an aqueous solution containing 5 μg of soybean trypsin. Next, the activity of mutant prourokinase contained in 105 μl of this reaction mixture was measured by the method described in (iv). Note, as control samples natural type prourokinase and a purified preparation of mutant prourokinase Q(135) D(157) were used. The results are shown in FIG. 12.

Figure 12:
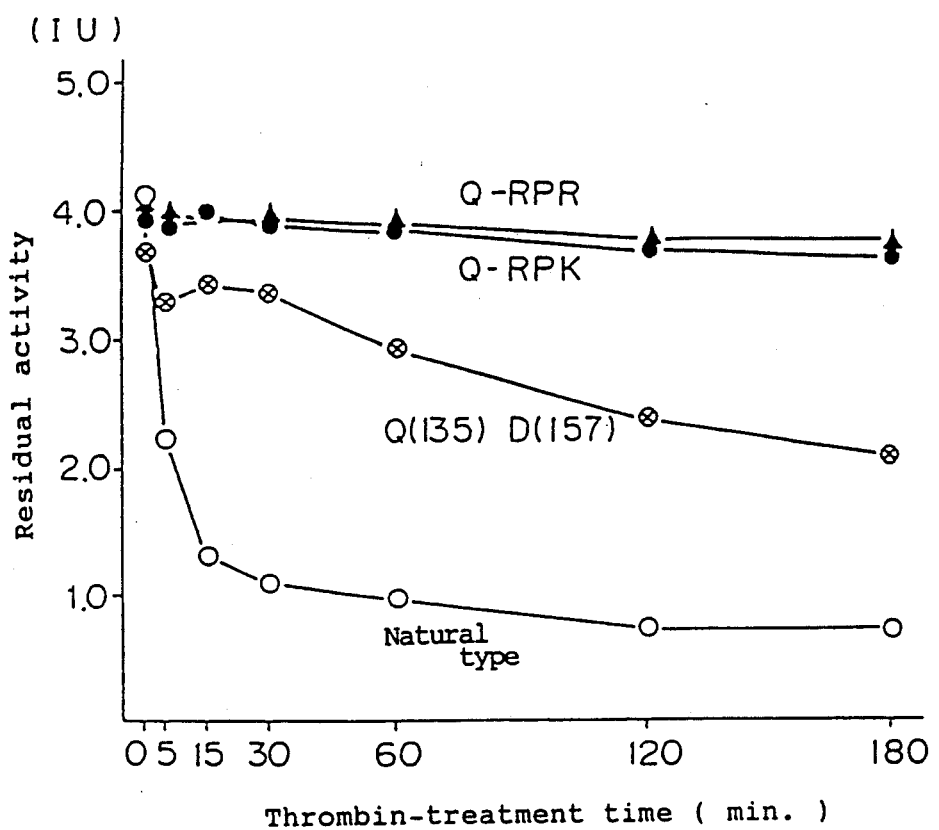
FIG. 12 shows the result when the residual activity of purified preparations of the present mutant prourokinases Q-RPK and Q-RPR after thrombin treatment is plotted in relation to the thrombin treatment time.

FIG. 12 shows that the mutant prourokinases Q-RPK and Q-RPR are, in contrast to natural type prourokinase and mutant prourokinase Q(135) D(157), little inactivated by thrombin.

(iv) Measurement of Activity of Activated Mutant Prourokinase by Synthetic Substrate S-2444

To 105 μl of the reaction mixtures obtained in (i), (ii) and (iii), 0.7 μl of 50 mM Tris-HCl (pH 8.0) solution containing 0.2 mM S-2444 (Daiichi Kagaku Yakuhin), 0.1 M sodium chloride and 0.01 % Triton X-100, and after reaction was carried out at 37° C. for 30 minutes, the reaction was terminated by adding 0.1 ml of acetic acid. Next, an increase of an absorbance at 405 nm for 30 minutes was measured, and the activity for the sample was calculated on the basis of a value for a urokinase standard (Nippon Soda K.K.) (increase of absorbance at 405 nm for 30 minutes is 0.0608 for one unit). The results are shown in FIGS. 10, 11, and 12. FIG. 10 shows that the mutant prourokinase Q-RPK and Q-RPR are, similar to natural type prourokinase and mutant prourokinase Q(135)D(157), activated by plasmin. FIG. 11 shows that the mutant prourokinase Q-RPK and Q-RPR are rapidly activated by thrombin. This property is an absolutely new property not found in natural type prourokinase and mutant prourokinase Q(135)D(157). FIG. 12 shows that the mutant prourokinase Q-RPK and Q-RPR are, in contrast to natural type prourokinase and the mutant prourokinase Q(135) D(157), little inactivated by thrombin.

Reference Example 1. (Construction of Starting Plasmid)

Starting with plasmid pKYU22 containing a cDNA coding for natural type human prourokinase, the structure of a 30 bp of the 5'-end portion of this naturally occurring cDNA was altered to permit the prourokinase gene to be efficiently expressed in *E. coli* under the SD sequence of the *Pseudomonas putida*-derived C230 gene.

*Escherichia coli* X1766 (pKYU22) containing plasmid pKYU22 was deposited as FERM BP-968, as an international deposition.

The following three single-chain DNA oligomers comprising 29, 15, and 20 nucleotides respectively were synthesized by the phosphotriester method:

```
5' CATGAGCAACGAGCTCCACCAGGTTCCGT 3'
3' TTGCAGTACTCGTTGC 5'
                3' TCGAGGTGGTCCAAGGCAGC 5'
```

Next, 1 μg each of the synthetic DNA oligomers was heated for 2 minutes at 95° C, phosphorylated at the 5'-end with T4 polynucleotide kinase and purified using a Sep Pak (C18) column (made by Waters). After drying, the purified material was dissolved in 50 μl of 20 mM Tris-HCL (pH 7.6) and 10 mM MgCl , and annealed by heating for 2 minutes at 95° C., cooling slowly to room temperature, and then maintaining the solution overnight at 12° C. to give the following double-stranded DNA:

```
5'     CATGAGCAACGAGCTCCACCAGGTTCCGT 3'
3' TGCAGTACTCGTTGCTCGAGGTGGTCCAAGGCAGC
   AatII          SstII      BstNI    TaqI
```

On the one hand, 5 μg of DNA of plasmid $_p$KYU22 was digested twice with restriction endonucleases BolII and AatII, and about 5.7 Kb DNA fragment was recovered by electric elution, and on the other hand, 5 μg of DNA of the same plasmid $_p$KYU22 was twice digested with restriction endonucleases PstI and BqlII and about 400 bp DNA fragment was obtained by electric elution method. This fragment was again digested with restriction endonucleases TaqI and about 260 bp DNA fragment was recovered by electric elution. These two different DNA fragments were recovered and purified by phenol/chloroform extraction, and precipitation with 2 volumes of ethanol.

The two different DNA fragments and the aforesaid double-stranded synthetic DNA oligomer were ligated together using T4DNA ligase and transformed into E. coli χ1776. Then the transformants were screened by the rapid isolation method by the alkali lysis procedure, and a clone Escherichia coli χ1776/pKMU1 carrying the plasmid pKMU1 that contains a modified prourokinase gene was obtained. The clone E. coli χ1776/pKYU1 has been deposited with the Fermentation Research Institute, Agency of Science and Technology as FERM P-8040.

Reference Example 2. Construction of Prourokinase Directly Expressive Plasmid (pMUT4L)

Five μg of plasmid KMU1 from Reference Example 1 was digested with 10 units of restriction endonuclease AatII and the digest was isolated after treatment with calf intestinal phosphatase (CIP). On the other hand, 5 μg of plasmid pTCM1 was digested with 10 units of restriction endonuclease AatII and about 500 bp DNA fragment was isolated by the electric elution method. These two different DNA fragments were purified by repeated phenol/chloroform extraction and ethanol precipitation.

Both of these DNA fragments were joined together using T4DNA ligase and were transformed into E. coli JM103. The transformants were screened by the rapid isolation method using the alkali lysis procedure, and a clone carrying plasmid pMUT1L in which tac promoter/ operator and C230SD sequence having the normal orientation with reference to the prourokinase gene was obtained.

Said plasmid pTCM1, which is a novel plasmid constructed by the present inventors, contains an expression controlling region comprising tac promoter/ operator, lac SD, C230SD sequences as well as the C230 structural gene. E. coli JM103/pTCM1 carrying said plasmid has been deposited with the Fermentation Research Institute, Agency of Science and Technology as FERM BP-1990 as an international deposition.

In plasmid MUT1L the modified prourokinase gene of the present invention is inserted at an appropriate site downstream of the expression controlling region comprising tac promoter/operator, lac SD and C230SD sequences.

Next, 5 μg of plasmid pKK223-3 (Literatures 22, 23 and 24) was digested with 10 units of restriction endonuclease HindIII, and the digest was treated with calf intestinal phosphatase (P.L. Biochemicals).

On the other hand, 1 μg of the resulting plasmid pMUT1L was digested with 4 units of restriction endonuclease DraI and the digestion fragment and 1 μg of 5'-phosphorylated HindIII linker (dCAAGCTTG) were ligated with T4DNA ligase. Digestion was carried out using 12 units of restriction endonuclease HindIII, and the digest was dissolved in 0.15 M NaCl. The solution was extracted with an equal volume of phenol/chloroform and the DNA was precipitated by the addition of 2 volumes of ethanol. The precipitate was collected at 16,000 rpm and at 4° C. and was dried.

The resultant pMUT1L digestion fragment and the HindIII digestion fragment of aforesaid pKK223-3 were ligated using T4 DNA ligase and were transformed into E. coli JM103. The transformants were screened by the alkali lysis procedure and a clone, E. coli JM103/pMUT2L containing plasmid pMUT2L was obtained.

This plasmid not only has said expression control region upstream from the prourokinase gene but also has a transcription terminator (rrnB, $T_1T_2$) of the E. coli ribosomal gene derived from pKK223-3 downstream therefrom.

Note, Plasmid pKK223-3 is readily obtainable as it is marketed by Pharmacia P-L Biochemicals.

Five μg of plasmid pMUT2L was digested with 10 units each of restriction endonucleases SphI and Tth111 I, and after extraction with phenol/chloroform DNA was precipitated with ethanol. The DNA thus recovered was blunt-ended using T4 polymerase in the presence of 0.1 mM dGTP, dCTP, dATP and TTP, and was recycled by T4 DNA ligase. The DNA was transformed into E. coli JM103 and colonies were allowed to form on an LB agar medium containing 50 μg/ml of ampicillin. The transformants were screened by the alkali lysis procedure (literature 14) and a clone, E. coli JM103/pMUT4L was obtained.

LITERATURE

1. Gurewich, V. et al.; J.Clin. Invest. 73, 1731 (1984).
2 Ichinose, A. et al. ; J. Biol. Chem. 261, 3486 (1986).
3. Kasai, S. et al. ; J. Biol. Chem. 260, 12382 (1985).
4. Liu, C.Y. et al. ; J. Biol. Chem. 254, 10421 (1979).
5. Kaminski, M. et al. ; J. Biol. Chem. 258, 10530 (1983).
6. Jui-Yoa Chang ; Eur. J. Biochem. 151, 217 (1985).
7. Japanese Patent Application No. 61-12984 (Japanese Unexamined Patent Publication No. 62-143686)

Referring to deposition of microorganism under Rule 13-2.

DEPOSITORY AUTHORITY: Fermentation Research Institute Agency of Industrial Science and Technology, Ministry of International Trade and Industry ADDRESS:1-3, Higashi 1-chome Tsukuba-shi Ibaraki-ken 305, Japan

DEPOSITION NUMBER AND DATE OF DEPOSITION:

1. FERM BP-1990 Aug. 17, 1984 (Transferred from FERM p-7779 on August 4, 1988)
2. FERM P-8040 Jan. 11, 1985
3. FERM BP-969 Jan. 11, 1985 (Transferred from FERM P-8042 on January 22, 1986)
4. FERM BP-970 Apr. 18, 1985 (Transferred from FERM P-8188 on January 22, 1986)
5. FERM BP-971 Jul. 11, 1985 (Transferred from FERM P-8341 on January 22, 1986)

DEPOSITORY AUTHORITY: Deutsche Sammulung von Microorganismen

ADDRESS: Grisebachstrasse 8, D-3400 Göttingen, Federal Republic of Germany

DEPOSITION NUMBER AND DATA OF DEPOSITION:

| | |
|---|---|
| 6. DSM 4186 | July 22, 1987 |
| 7. DSM 4187 | July 22, 1987 |
| 8. DSM 4188 | July 22, 1987 |
| 9. DSM 4189 | July 22, 1987 |

We claim:

1. A human prourokinase-like polypeptide having the following amino acid sequence:

$$(Met)\cdot Ser^1 \ldots\ldots X^{156}.Y^{157}.Z^{158}-$$

wherein Met is an optionally present methionine; $Ser^1$ is the first N-terminal serine; $X^{156}.Y^{157}.Z^{158}$ is an amino acid sequence from the 156th amino acid to the 158th amino acid and is selected from the group consisting of Arg.Pro.Lys, Arg.Pro.Arg, and Cln,Pro.Arg; the dotted line represents an amino acid sequence from the second amino acid to the 155th amino acid of native human prourolinase wherein the 135th Lys is optionally replaced by an amino acid selected from the group consisting of Asn and Gln,; and the solid line represents an amino acid sequence from the 159th amino acid to the C-terminal of the native human prourokinase; or substantially the same amino acid sequence as the above-mentioned amino acid sequence.

2. A polypeptide according to claim 1, wherein the amino acid sequence of the native human prourokinase is an amino acid sequence encoded by cDNA corresponding to mRNA derived from human kidney.

3. A pharmaceutical preparation comprising a human prourokinase polypeptide having the following amino acid sequence:

$$(Met)\cdot Ser^1 \ldots\ldots X^{156}.Y^{157}.Z^{158}-$$

wherein Met is an optionally present methionine; $Ser^1$ is the first N-terminal serine; $X^{156}.Y^{157}.Z^{158}$ is an amino acid sequence from the 156th amino acid to the 158th amino acid and is selected from the group consisting of Arg.Pro.Lys, Arg.Pro.Arg, and Gln.Pro.Arg; the dotted line represents an amino acid sequence from the second amino acid to the 155th amino acid of native human prourokinase wherein the 135th Lys is optionally replaced by an amino acid selected from the group consisting of Asn and Gln,; and the solid line represents an amino acid sequence from the 159th amino acid to the C-terminal of the native human prourokinase; or substantially the same amino acid sequence as the above-mentioned amino acid sequence.

4. Method for the prophylaxis or treatment of thrombus formation, characterized by administering to a patient a human prourokinase-like polypeptide having the following amino acid sequence:

$$(Met)\cdot Ser^1 \ldots\ldots X^{156}.Y^{157}.Z^{158}-$$

wherein Met is an optionally present methionine; $Ser^1$ is the first N-terminal serine; $X^{156}.Y^{157}.Z^{158}$ is an amino acid sequence from the 156th amino acid to the 158th amino acid and is selected from the group consisting of Arg.Pro.Lys, Arg.Pro.Arg, and Gln.Pro.Arg; the dotted line represents an amino acid sequence from the second amino acid to the 155th amino acid of native human prourokinase wherein the 135th Lys is optionally replaced by an amino acid selected from the group consisting of Asn and Gln,; and the solid line represents an amino acid sequence from the 159th amino acid to the C-terminal of the native human prourokinase; or substantially the same amino acid sequence as the above-mentioned amino acid sequence.

* * * * *